(12) United States Patent
Kozlov et al.

(10) Patent No.: US 8,101,375 B2
(45) Date of Patent: Jan. 24, 2012

(54) COMPOSITIONS AND METHODS FOR DETECTING PHOSPHOMONOESTER

(75) Inventors: Igor Kozlov, San Diego, CA (US); Peter Melnyk, San Diego, CA (US); Chanfeng Zhao, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 12/868,524

(22) Filed: Aug. 25, 2010

(65) Prior Publication Data

US 2011/0020853 A1 Jan. 27, 2011

Related U.S. Application Data

(63) Continuation of application No. 11/298,907, filed on Dec. 9, 2005, now Pat. No. 7,803,751.

(51) Int. Cl.
*C12Q 1/48* (2006.01)
(52) U.S. Cl. .......................... 435/15; 435/68.1; 530/409
(58) Field of Classification Search .................. None
See application file for complete search history.

(56) References Cited

U.S. PATENT DOCUMENTS

| | | | |
|---|---|---|---|
| 5,512,486 | A | 4/1996 | Giese et al. |
| 5,686,310 | A | 11/1997 | Haystead et al. |
| 6,200,737 | B1 | 3/2001 | Walt et al. |
| 6,355,431 | B1 | 3/2002 | Chee et al. |
| 6,429,027 | B1 | 8/2002 | Chee et al. |
| 6,713,602 | B1 | 3/2004 | Burchardt et al. |
| 2002/0049307 | A1 | 4/2002 | Aebersold et al. |
| 2002/0102578 | A1 | 8/2002 | Dickinson et al. |
| 2003/0134303 | A1 | 7/2003 | Campbell et al. |
| 2004/0125424 | A1 | 7/2004 | Moon et al. |
| 2004/0132205 | A1 | 7/2004 | Moon et al. |
| 2004/0171034 | A1* | 9/2004 | Agnew et al. ...................... 435/6 |
| 2004/0233485 | A1 | 11/2004 | Moon et al. |
| 2004/0263923 | A1 | 12/2004 | Moon et al. |
| 2005/0014197 | A1 | 1/2005 | Agnew et al. |
| 2005/0043507 | A1 | 2/2005 | Campbell et al. |
| 2005/0048667 | A1 | 3/2005 | Ellman et al. |
| 2005/0136406 | A1 | 6/2005 | Kozlov et al. |
| 2006/0216721 | A1 | 9/2006 | Kozlov et al. |

FOREIGN PATENT DOCUMENTS

| | | |
|---|---|---|
| WO | WO 98/40726 | 9/1998 |
| WO | WO 98/50782 | 11/1998 |
| WO | WO 00/60332 | 10/2000 |
| WO | WO 00/63437 | 10/2000 |
| WO | WO 01/41918 | 6/2001 |
| WO | WO 02/00336 | 1/2002 |
| WO | WO 03/002979 | 1/2003 |
| WO | WO 04/001646 | 12/2003 |

OTHER PUBLICATIONS

Adamczyk, M. et al., "Selective analysis of phosphopeptides within a protein mixture by chemical modification, reversible biotinylation and mass spectrometry," Rapid Communications in Mass Spectrometry, 15:1481-1488 (2001).

Akita, S. et al., "On-Bead Fluorescence Assay for Serine/Threonine Kinases," Organic Letters, 7(25):5565-5568 (2005).
Andersen, J. et al., "Structural and Evolutionary Relationships among Protein Tyrosine Phosphatase Domains," Molecular and Cellular Biology, 21(21):7117-7136 (2001).
Angeles, T. et al., "Enzyme-Linked Immunosorbent Assay for trkA Tyrosine Kinase Activity," Analytical Biochemistry, 236:49-55 (1996).
Byford, M., "Rapid and selective modification of phosphoserine residues catalysed by Ba2+ ions for their detection during peptide microsequencing.," Biochem, J., 280:261-265 (1991).
Dolinnaya, N. et al., "Structural and kinetic aspects of chemical reactions in DNA duplexes. Information on DNA local structure obtained from chemical ligation data," Nucleic Acids Research, 19(11):3073-3080 (1991).
Goshe, M. et al., "Phosphoprotein Isotope-Coded Affinity Tag Approach for Isolating and Quantitating Phosphopeptides in Proteome-Wide Analyses," Analytical Chemistry, 73:2578-2586 (2001).
Knight, Z. et al., "Phosphospecific proteolysis for mapping sites of protein phosphorylation," Nature Biotechnology, 21(9):1047-1054 (2003).
Manning, G. et al., "The Protein Kinase Complement of the Human Genome," Science, 298:1912-1934 (2002).
Meyer, et al., "Sequence analysis of phophoserine-containing peptides," FEBS Letters, 204(1):61-66 (1986).
Hoare et al., "A Method for the Quantitative Modification and Estimation of Carboxylic Acid Groups in Proteins," Journal of Biological Chemistry, 242(10): 2447-2453 (1967).
Molloy, M. et al., "Phosphopeptide Derivatization Signatures to Identify Serine and Threonine Phosphorylated Peptides by Mass Spectrometry," Analytical Chemistry, 73(22):5387-5394 (2001).
Nielsen, P. et al., "Sequence-Selective Recognition of DNA by Strand Displacement with a Thymine-Substituted Polyamide," Science, 254:1497-1500 (1991). Oda, Y. et al., "Enrichment analysis of phosphorylated proteins as a tool for probing the phosphoproteome," Nature Biotechnology, 19:379-382 (2001).
Ortutay, C. et al., "KinMutBase: A Registry of Disease-Causing Mutations in Protein Kinase Domains," Human Mutation, 25:435-442 (2005).
Simpson, D. et al., "β-Elimination and Sulfite Addition as a Means of Localization and Identification of Substituted Seryl and Threonyl Residues in Proteins and Proteoglycans," Biochemistry, 11(10):1849-1856 (1972).

(Continued)

*Primary Examiner* — Christopher R. Tate
*Assistant Examiner* — Roy Teller
(74) *Attorney, Agent, or Firm* — John T. Murphy

(57) ABSTRACT

The invention provides a method of modifying a phosphomonoester moiety of a target compound. The method can include the steps of (a) providing a target compound having an electrophilic moiety and a phosphomonoester moiety; (b) contacting the target compound with a first carbodiimide compound under conditions for preferential addition of the first carbodiimide compound to the electrophilic moiety over the phosphomonoester moiety, thereby forming an electrophile-protected target compound; and (c) contacting the electrophile-protected target compound with a second carbodiimide compound and a nucleophilic compound under conditions for addition of the nucleophilic compound to the phosphomonoester.

20 Claims, 12 Drawing Sheets

OTHER PUBLICATIONS

Toniolo, C. et al., "*N*-Acylureas in Peptide Synthesis: An X-Ray Diffraction and IR-Absorption Study," Helvetica Chimica Acta, 73(3):626-634 (1990).

Tung, C., "Preparation & Applications of Peptide-Oligonucleotide Conjugates," Bioconj. Chem., 11:605-618 (2000).

Witt, J. et al., "Rapid Protein Kinase Assay Using Phosphocelluloase-Paper Absorption," Analytical Biochemistry, 66:253-258 (1975).

Wu, J. et al., "Identification of a High-Affinity Anti-Phosphoserine Antibody for the Development of a Homogeneous Fluorescence Polarization Assay of Protein Kinase C," Journal of Biomolecular Screening, 5(1):23-30 (2000).

Zhou, H. at al., "A systematic approach to the analysis of protein phosphorylation," Nature Biotechnology, 19:375-378 (2001).

Zubin, E. at al., "Modern methods for the synthesis of peptide-oligonucleotide conjugates," Russian Chemical Reviews, 71(3):239-264 (2002).

\* cited by examiner

| Cross-reactivity | p60 Enzyme | PKA Enzyme |
|---|---|---|
| p60 substrate | 100% | <1% |
| PKA substrate | <1% | 100% |

| Inhibition Efficiency | Without inhibitor | With PKA inhibitor | With p60 inhibitor |
|---|---|---|---|
| Kinase activity | | | |
| PKA enzyme | 0% | >99% | 0% |
| p60 enzyme | 0% | 0% | 85% |

FIG. 6

COMPOSITIONS AND METHODS FOR DETECTING PHOSPHOMONOESTER

This application is a continuation of U.S. Ser. No. 11/298,907, filed Dec. 9, 2005, now U.S. Pat. No. 7,803,751, the entire disclosure of which is incorporated herein by reference.

This invention was made with government support under grant number 1 R43 GM071272-01A1 awarded by the National Institute of Health. The United States Government has certain rights in this invention.

BACKGROUND OF THE INVENTION

This invention relates generally to analysis of phosphorylated compounds, and more specifically to detecting phosphorylation of biological molecules.

The cells of all organisms are capable of evaluating changes in their environment and appropriately altering function for an appropriate response. The responses are mediated by signal transduction systems that convert external stimuli into internal biochemical signals. These signal transduction systems share several characteristics across a wide variety of organisms whether single cell organisms such as bacteria or multicellular organisms such as animals and plants. Typically, a specific cellular receptor changes from one state to another due to a particular environmental stimulus and this change in state initiates a series of biochemical reactions that lead to one or more functional responses of the cell to the stimulus. For example, the presence of a particular nutrient, toxin or hormone can be detected by a cell leading to a change in cellular function allowing uptake and metabolism of the nutrient, sequestration and breakdown of the toxin or changes in growth and development, respectively.

One of the most widely used biochemical reactions of the signal transduction pathways of a wide variety of organisms is the transfer of a phosphate residue onto a biological target molecule in such a way that the function of the target molecule is changed. The addition of phosphates is mediated by kinases. Typically, a series of protein kinases act to sequentially activate each other by phosphorylation until ultimately the pathway reaches an enzyme that, when phosphorylated, changes its function to adapt the cell to the initial stimulus that activated the signal transduction pathway.

Signal transduction pathways that utilize phosphorylation play critical roles in a multitude of cellular functions including cell homeostasis, differentiation, development and growth. Improper function or response of signal transduction pathways have been found to play important roles in a variety of diseases and conditions including, for example, cancer, allergic responses, autoimmune diseases and degenerative diseases. In addition, the efficacy of many therapeutic drugs is due to their ability to alter particular signal transduction pathways.

The ability to monitor the states of phosphorylation for specific biochemical molecules can provide an understanding of many fundamental biological processes, for example, in a research setting. This can also be beneficial in a clinical setting for the diagnosis of various diseases or conditions, or for the prognosis of individuals being treated for a particular disease or condition. Furthermore, the ability to monitor phosphorylation can be valuable for the design or identification of therapeutic drugs that target specific kinases or signal transduction pathways.

Currently, several technologies are available for analyzing and detecting phosphorylation of biological molecules. One of the most widely used methods is to treat a test sample with ATP containing radioactive γ-phosphate followed by evaluating incorporation of radioactivity into a target component of interest. In many cases, the use of radioactivity is undesirable due to safety concerns, the cost of preparing and handling radioactive material and the environmental impacts of radioactivity disposal. Radioactivity can be avoided by using a phospho-specific antibody to detect a phosphorylated target component. However, the ability of these antibodies to detect a phosphate residue is dependent upon the chemical composition of the component to which the phosphate residue is attached. In many cases a new antibody must be generated for each different target to be detected. This can lead to difficulties when dealing with biological targets for which the exact composition is unknown. Even when targets of known composition are used, the need to generate and evaluate different antibodies for each target can be both time consuming and expensive.

Thus, there exists a need for a method of detecting phosphorylation of biological targets that is safe, effective and widely applicable to targets having any of a variety of different chemical compositions. The present invention satisfies this need and provides other advantages as well.

BRIEF SUMMARY OF THE INVENTION

The invention provides a method of modifying a phosphomonoester moiety of a target compound. The method can include the steps of (a) providing a target compound having an electrophilic moiety and a phosphomonoester moiety; (b) contacting the target compound with a first carbodiimide compound under conditions for preferential addition of the first carbodiimide compound to the electrophilic moiety over the phosphomonoester moiety, thereby forming an electrophile-protected target compound; and (c) contacting the electrophile-protected target compound with a second carbodiimide compound and a nucleophilic compound under conditions for addition of the nucleophilic compound to the phosphomonoester.

The invention further provides a method of modifying a phosphomonoester moiety of a target compound. The method can include the steps of (a) providing a target compound having a carboxylic acid moiety and a phosphomonoester moiety; (b) contacting the target compound with a first carbodiimide compound under conditions for preferential addition of the first carbodiimide compound to the carboxylic acid moiety over the phosphomonoester moiety, thereby forming a carboxyl-protected target compound; and (c) contacting the carboxyl-protected target compound with a second carbodiimide compound and an amine under conditions for addition of the amine to the phosphomonoester.

The invention further provides a method of detecting a phosphomonoester moiety of a target compound. The method can include the steps of (a) providing a target compound having a carboxylic acid moiety and a phosphomonoester moiety; (b) contacting the target compound with a first carbodiimide compound under conditions for preferential addition of the first carbodiimide compound to the carboxylic acid moiety over the phosphomonoester moiety, thereby forming a carboxyl-protected target compound; (c) contacting the carboxyl-protected target compound with a second carbodiimide compound and an amine under conditions for addition of the amine to the phosphomonoester moiety, thereby forming a nucleophile-modified phosphate moiety; and (d) detecting the nucleophile-modified phosphate moiety.

and for carbodiimide-activated addition of an amino-containing dye to phosphomonoester moiety (reaction B).

Figure 2:
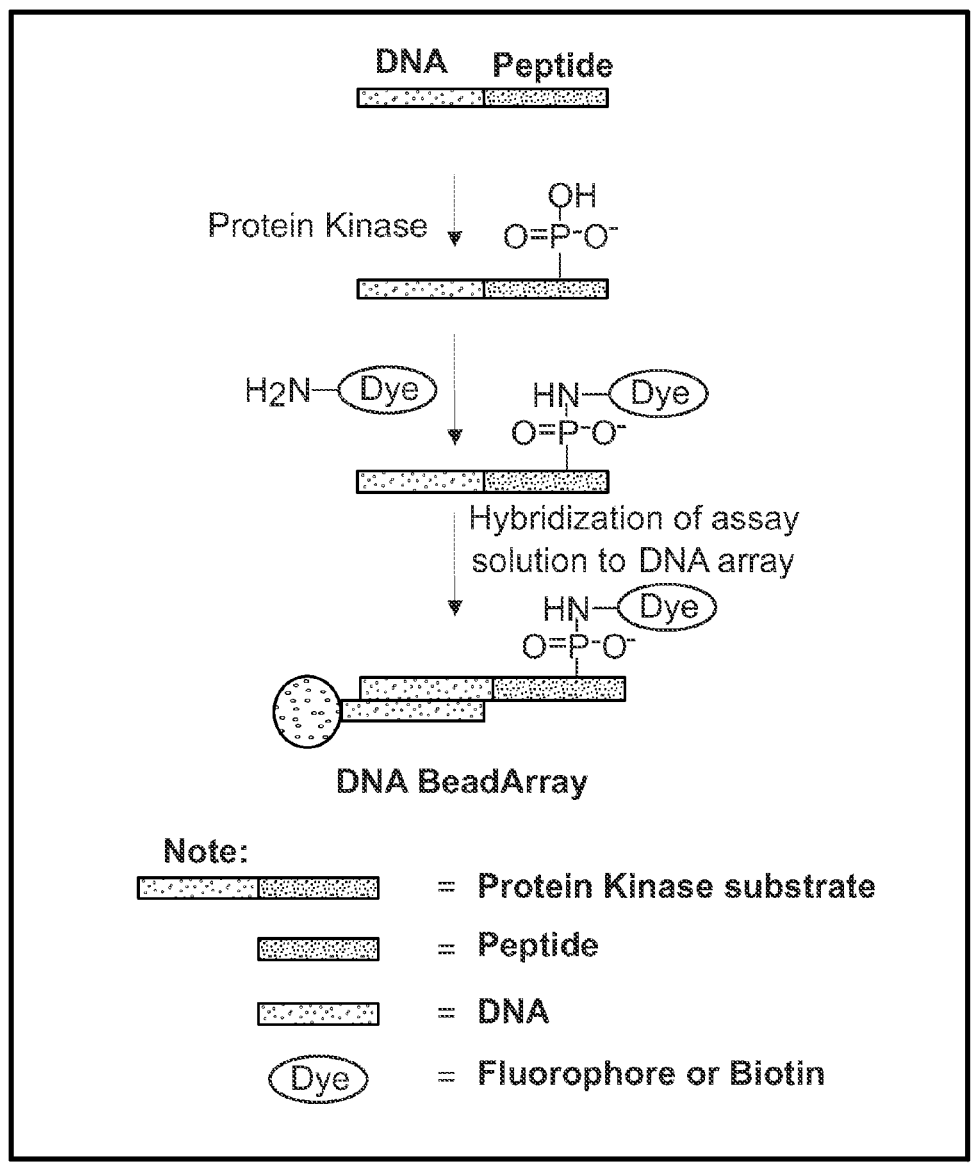

FIG. 2 shows a schematic representation of a kinase assay.

Figure 3:
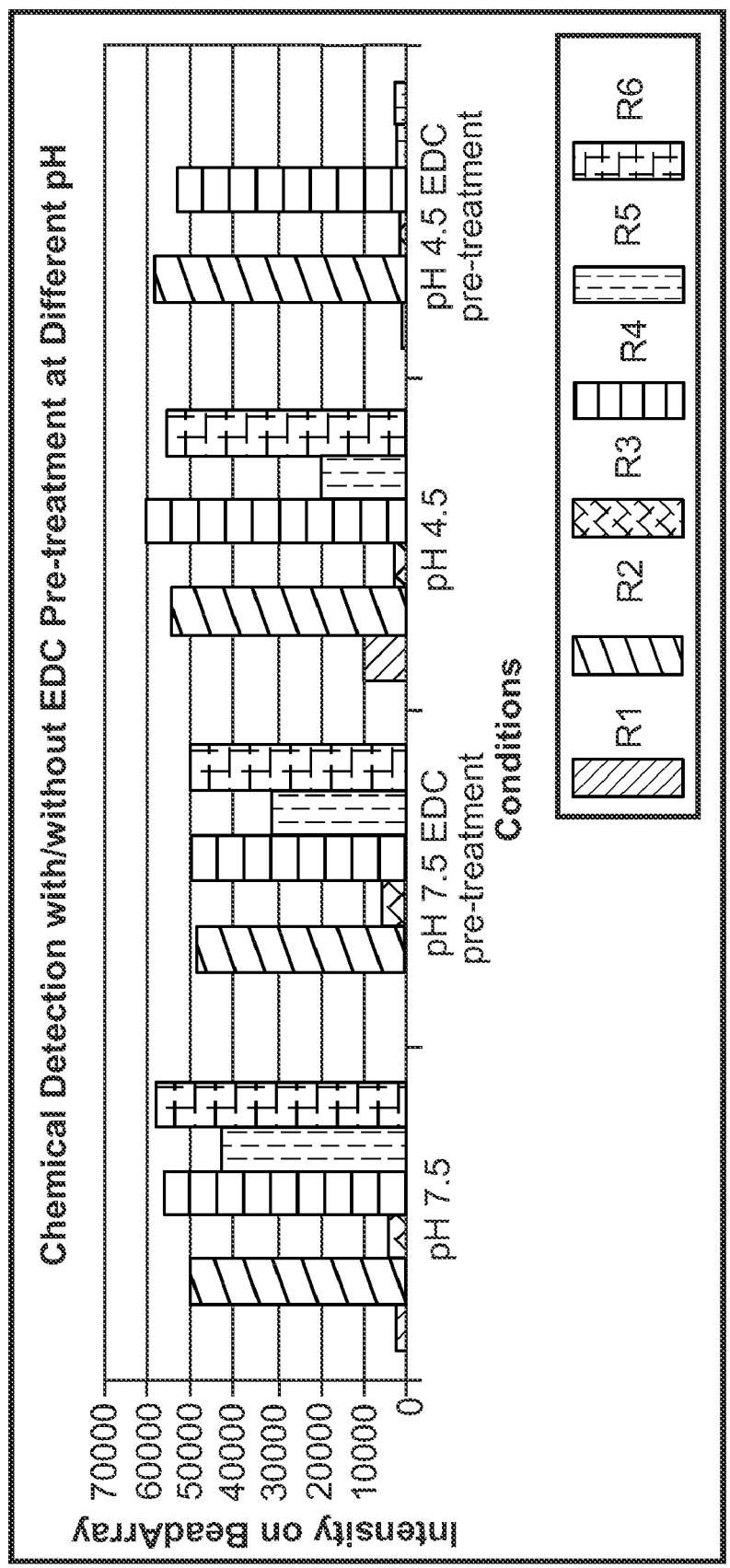

FIG. 3 shows a bar graph of signal intensities for different target compounds detected by EDC activated addition of an amino-containing dye following blocking of carbonyl moieties by EDC pre-treatment.

Figure 4A:
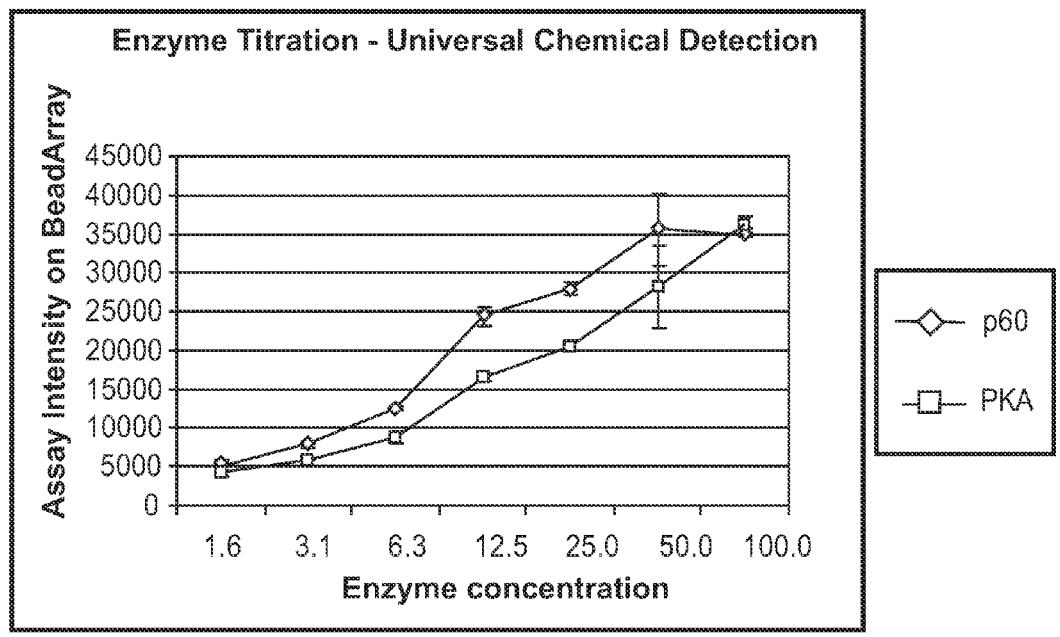
Figure 4B:
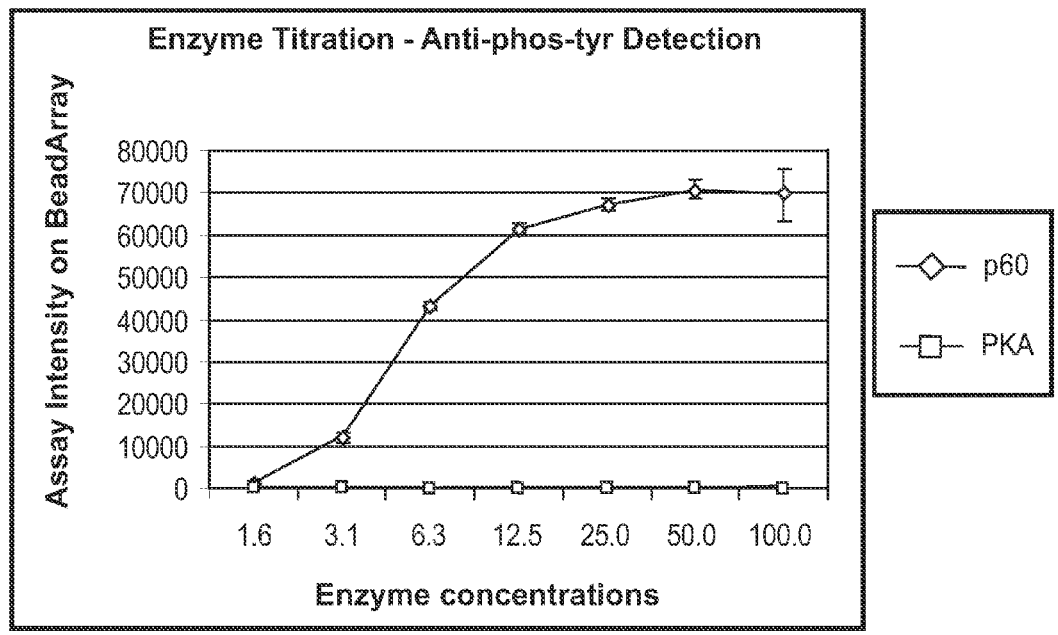
Figure 4C:
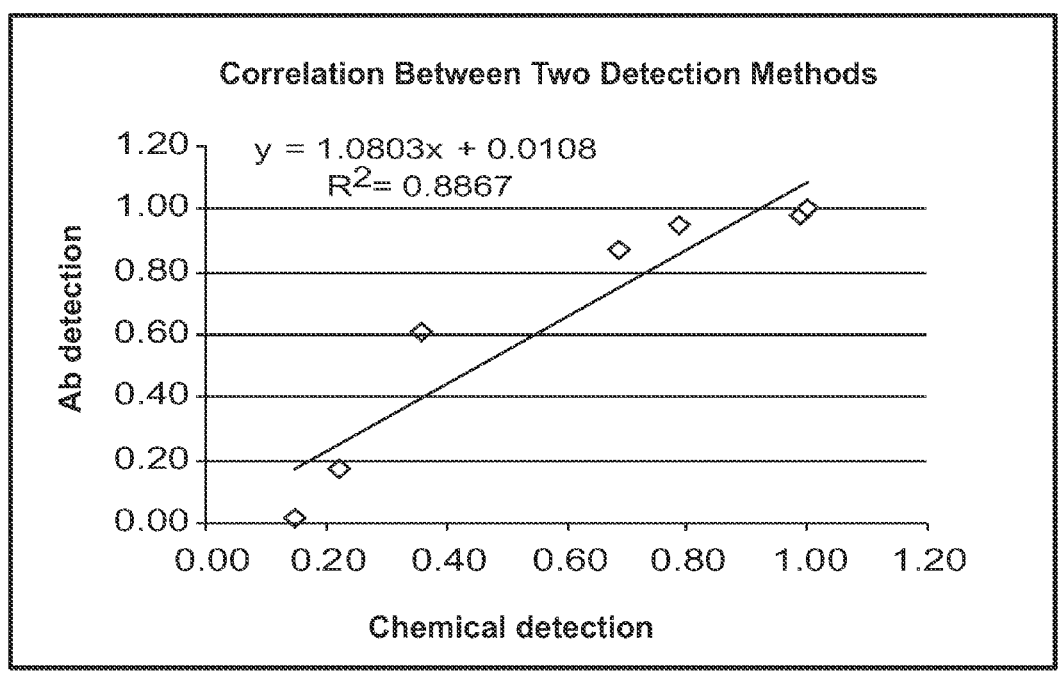

FIG. 4 shows results for phosphorylation of target proteins by p60c-src kinase and PKA kinase detected by chemical labeling (Panel A) or antibody-based labeling (Panel B); correlation of the two labeling approaches is also shown (Panel C).

Figure 5A:
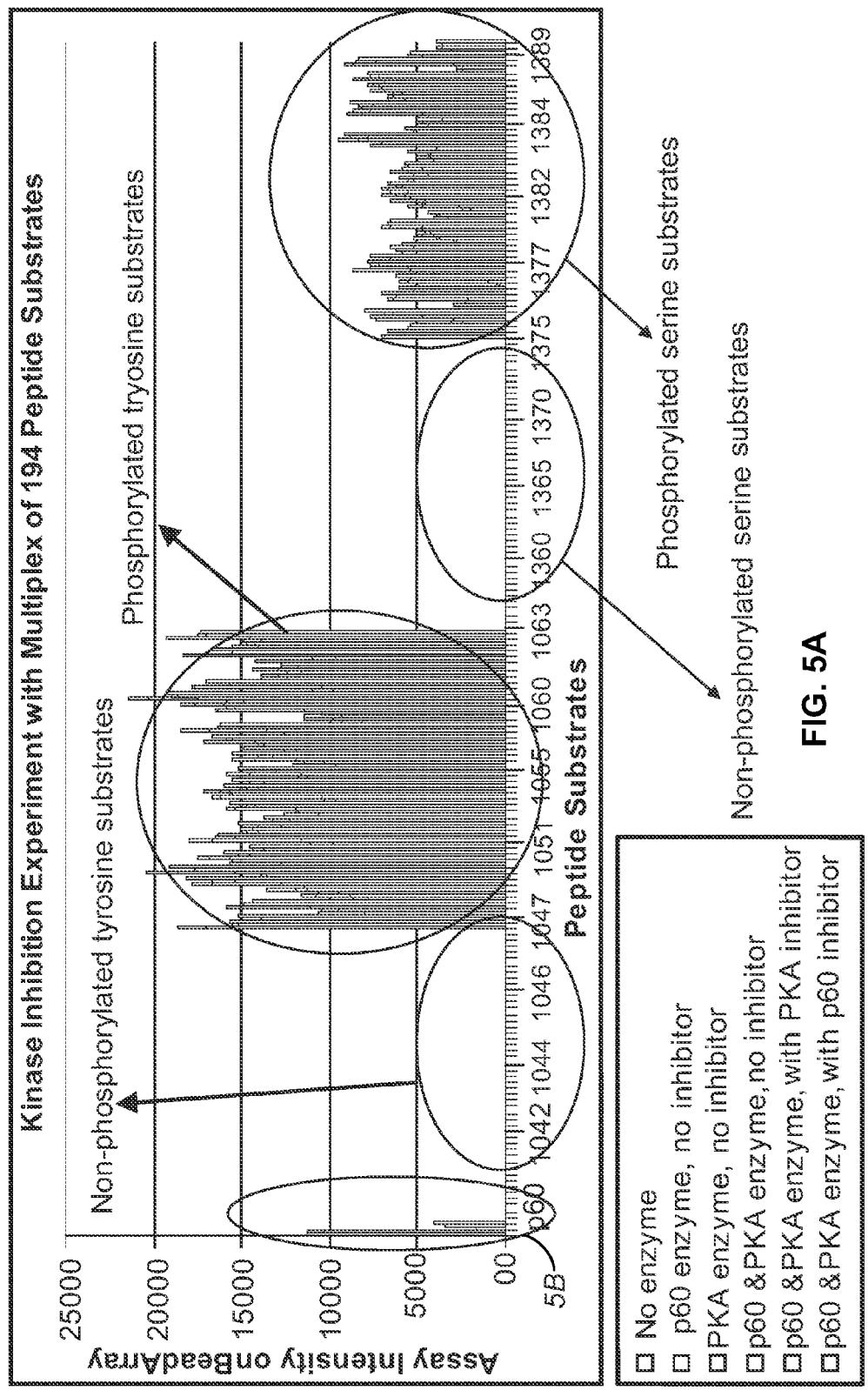
Figure 5B:
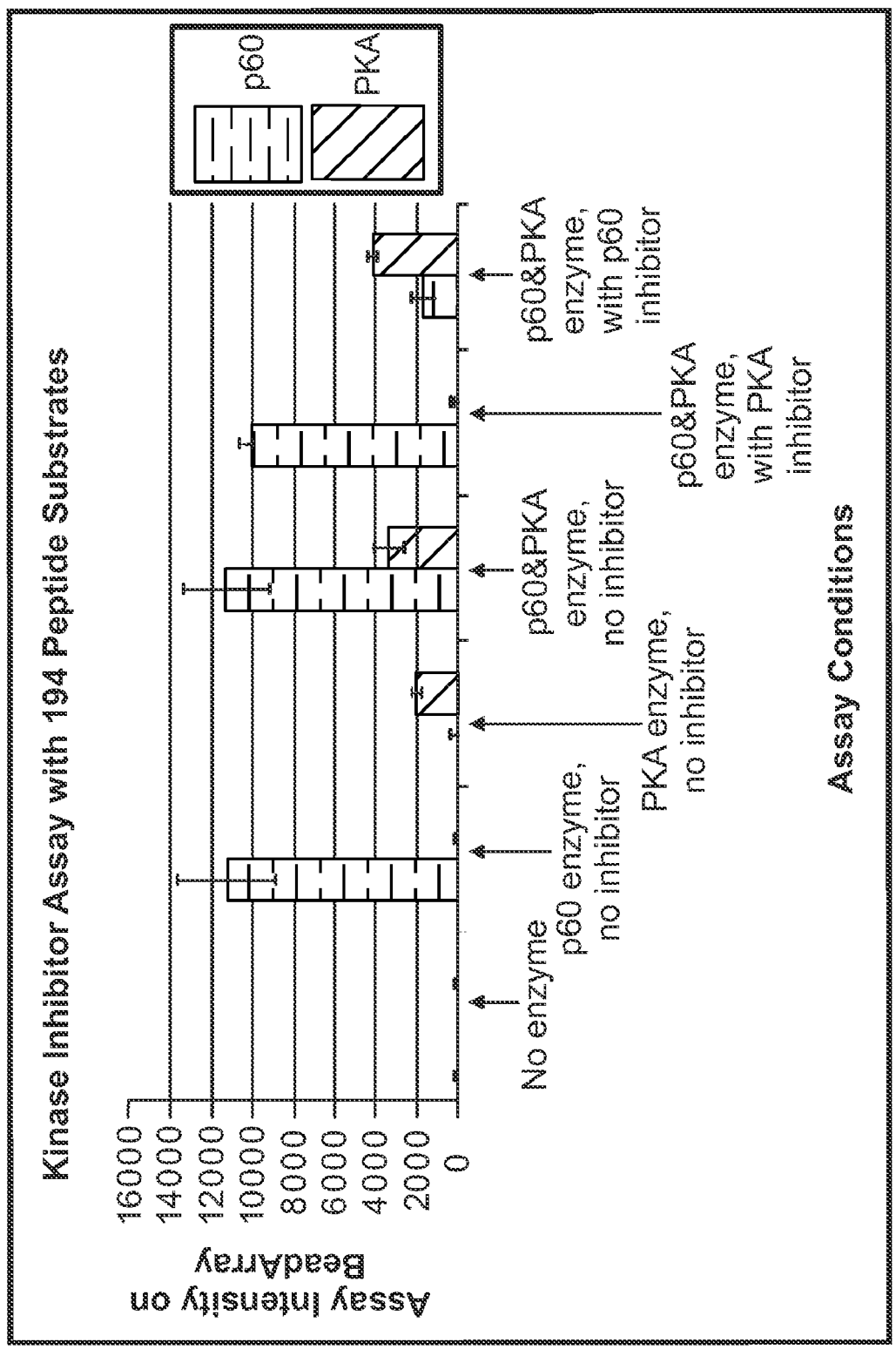

FIG. 5 shows a bar graph of kinase activity data for p60c-src and PKA kinases in a multiplex assay having 194 different protein-DNA targets, including substrates for various kinases, and in the presence or absence of inhibitors (Panel A) and an expanded view of a region of the bar graph showing kinase activity in the presence and absence of kinase inhibitors (Panel B).

FIG. 6 shows a table of results comparing cross reactivity and inhibition efficiency for assay of p60c-src kinase and PKA kinase in a multiplex assay having a pool of 194 different protein-DNA targets, including substrates for various kinases.

FIG. 7 shows signal measured for each of 96 different protein-DNA targets when treated with p60c-src kinase (Panel A) and PKA kinase (Panel B) in multiplex assays.

FIG. 8 shows bar graphs of results for kinase assays of 96 different protein-DNA targets when treated with p60c-src kinase and detected using antibody labeling (Panel A) or chemical labeling (Panel B).

Figure 9:
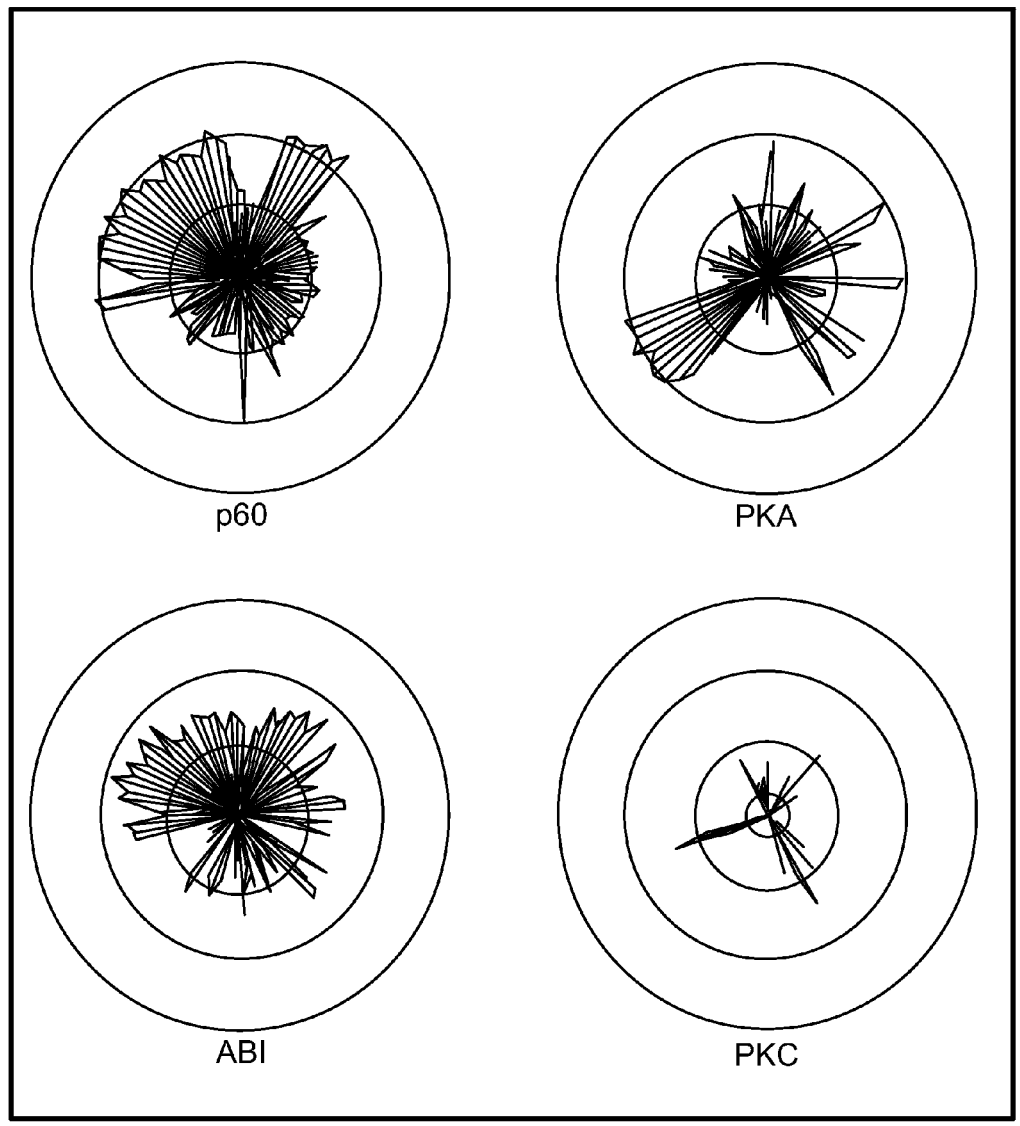

FIG. 9 shows star plots of the phosphorylation of 96 different protein-DNA kinase targets by the kinases p60c-src, PKA, Abl and PKC.

Figure 10:
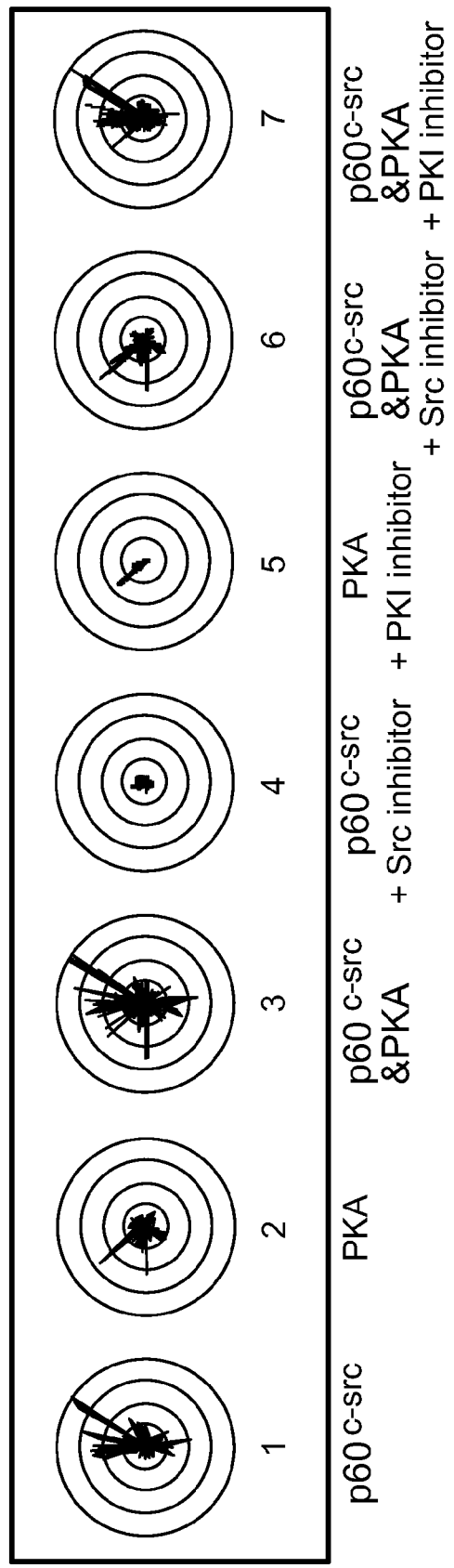

FIG. 10 shows star plots of the performance of 96 different protein-DNA targets in the presence of selective inhibitors.

DETAILED DESCRIPTION OF THE INVENTION

This invention provides methods for specifically modifying a phosphomonoester moiety of a target compound using carbodiimide chemistry. The method can include a step of protecting other electrophilic moieties in the target compound and is, therefore, well suited to modification of target compounds having other electrophilic moieties and/or target compounds in samples having such electrophilic moieties. An advantage of the methods is that both steps utilize carbodiimide chemistry and can be carried out in a one pot reaction. Thus, the target compound need not be separated from reagents used for the electrophile-protection step prior to modifying the phosphomonoester moiety.

The invention further provides the ability to modify a phosphomonoester moiety for detection of the phosphorylation state of a target compound. In particular embodiments, the methods can be used to determine activity of a kinase or phosphatase. The activity can be determined from the phosphorylation state of a target compound that is treated with a kinase or phosphatase.

An advantage of the methods is that modification or detection can be applied to target compounds having any of a variety of different chemical compositions. Thus, in embodiments where the target compounds are proteins, the methods can be used to determine the phosphorylation state of protein targets in a manner that is independent of differences in the amino acid sequences of the different proteins.

The invention is well suited to multiplex formats. Thus, a method of the invention can be used to modify a plurality of target compounds having phosphomonoester moieties. Furthermore, a plurality of target compounds modified in a method of the invention can be detected in a multiplex format. For example, a mixture of target compounds can be treated with a mixture of kinases, phosphatases or both, resulting in a mixture of target compounds having phosphomonoester moieties and the phosphomonoester moieties can be modified to produce a mixture of phosphate-modified target compounds that can be detected.

The invention can be used for any of a variety of purposes, such as the diagnosis of disease; determination of the response of cells to an external agent, such as a drug; staging of a disease, such as neoplasia; identifying cell differentiation or maturation; identifying new target compounds, identifying kinases or phosphatases present in a sample; screening for drugs that target a kinase or phosphatase, determining potential side effects of a drug; determining selectivity of a drug or the like.

DEFINITIONS

As used herein, the term "compound" is intended to mean a combination of two or more atoms held together by chemical bonds. A compound can include several moieties having the same or different properties such as structure, reactivity with a particular reagent or ability to generate a detectable signal. An exemplary compound useful in the invention is a target compound that is modified, detected or manipulated or for which modification, detection or manipulation is desired. A target compound can be made or used as a discrete compound or as a part of a larger molecule or complex. Exemplary target compounds include, but are not limited to, a molecule, polymer, protein or nucleic acid and can be bioactive, naturally occurring, non-naturally occurring or synthetic.

As used herein, the term "protein" is intended to mean a chain of amino acids connected by peptide bonds. The term is intended to include chains having any possible number of amino acids, unless explicitly indicated otherwise. Accordingly a protein can include a single linear chain having at least about 2, 3, 4, 5, 6, 7, 8, 9, 10, 15, 20, 25, 50, 100, 1,000, 10,000, 100,000 or more amino acids. If desired, a protein useful in the invention can have a maximum length including, for example, at most about 100,000, 10,000, 1,000, 100, 10, 5 or fewer in a linear chain. A protein can include one or more of the 20 amino acids used by a human cell to translate RNA into protein. Furthermore, a protein can include other amino acids such as non-naturally occurring amino acids. A "species" of proteins or protein moieties is understood to be a group that all include the same sequence of amino acids.

As used herein, the term "nucleic acid" is intended to mean a polymer molecule composed of subunits having purine or pyrimidine bases. A nucleic acid useful in the present invention will generally contain phosphodiester bonds, and can include, for example, DNA or RNA. If desired to suit a particular application, DNA or RNA analogs having alternate backbones can be used, including, for example, phosphoramide (Beaucage et al., *Tetrahedron* 49(10): 1925 (1993) and references therein; Letsinger, *J. Org. Chem.* 35:3800 (1970); Sprinzl et al., *Eur. J. Biochem.* 81:579 (1977); Letsinger et al., *Nucl. Acids Res.* 14:3487 (1986); Sawai et al, *Chem. Lett.* 805 (1984), Letsinger et al., *J. Am. Chem. Soc.* 110:4470 (1988); and Pauwels et al., *Chemica Scripta* 26:141 91986)), phosphorothioate (Mag et al., *Nucleic Acids Res.* 19:1437 (1991); and U.S. Pat. No. 5,644,048), phosphorodithioate (Briu et al., *J. Am. Chem. Soc.* 111:2321 (1989), O-methylphosphoroamidite linkages (see Eckstein, *Oligonucleotides and Analogues: A Practical Approach*, Oxford University Press), or peptide nucleic acid linkages (see Egholm, *J. Am. Chem. Soc.* 114:1895 (1992); Meier et al., *Chem. Int. Ed. Engl.* 31:1008 (1992); Nielsen, *Nature,* 365:566 (1993); Carlsson et al., *Nature* 380:207 (1996), all of which are incorporated by reference). Other polynucleotide analogs include those with positive backbones (Denpcy et al., *Proc. Natl. Acad. Sci. USA* 92:6097 (1995); non-ionic backbones (U.S. Pat. Nos. 5,386, 023, 5,637,684, 5,602,240, 5,216,141 and 4,469,863; Kiedrowski et al., *Angew. Chem. Intl. Ed. English* 30:423 (1991); Letsinger et al., *J. Am. Chem. Soc.* 110:4470 (1988); Letsinger et al., *Nucleoside & Nucleotide* 13:1597 (1994); Chapters 2 and 3, *ASC Symposium Series* 580, "Carbohydrate Modifications in Antisense Research", Ed. Y. S. Sanghui and P. Dan Cook; Mesmaeker et al., *Bioorganic & Medicinal Chem. Lett.* 4:395 (1994); Jeffs et al., *J. Biomolecular NMR* 34:17 (1994); *Tetrahedron Lett.* 37:743 (1996)) and non-ribose backbones, including those described in U.S. Pat. Nos. 5,235,033 and 5,034,506, and Chapters 6 and 7, *ASC Symposium Series* 580, "Carbohydrate Modifications in Antisense Research", Ed. Y. S. Sanghui and P. Dan Cook. Nucleic acids containing one or more carbocyclic sugars can also be used in the invention (see Jenkins et al., *Chem. Soc. Rev.* (1995) pp 169-176). Several other nucleic acid analogs are described in Rawls, *C & E News* Jun. 2, 1997 page 35. Each of the above-cited references is hereby incorporated by reference A nucleic acid can be single stranded, double stranded or contain portions of both double stranded and single stranded sequence. A polynucleotide can be DNA, RNA or a hybrid containing any combination of deoxyribo- and ribo-nucleotides or any combination of bases, including uracil, adenine, thymine, cytosine, guanine, inosine, xanthanine, hypoxanthanine, isocytosine, isoguanine, or the like. A "species" of nucleic acids or nucleic acid moieties is understood to be a group that all include the same nucleic acid sequence.

As used herein, the term "carboxylic acid moiety" is intended to mean a part of a compound having a carbon atom singly bonded to another atom of the compound, doubly bonded to a first oxygen atom and singly bonded to a second oxygen atom, wherein the second oxygen atom is negatively charged (O—) or bonded to a hydrogen as a hydroxyl moiety (OH). Exemplary carboxylic acid moieties that can be found in a protein include the alpha carboxylic acid moiety of the C-terminal amino acid of the protein, the beta carboxylic acid moiety of aspartate or the gamma carboxylic acid moiety of glutamate.

As used herein, the term "electrophile-protected," when used in reference to a compound, is intended to mean a compound for which an electrophilic moiety has been removed or modified to reduce or prevent reactivity toward a nucleophilic reagent. An exemplary electrophile-protected moiety is a carboxyl-protected moiety.

As used herein, the term "carboxyl-protected," when used in reference to a compound, is intended to mean a compound for which a carboxylic acid moiety has been removed or modified to reduce or prevent reactivity toward a carboxylic acid-reactive reagent. In particular embodiments, a carboxyl-protected moiety includes a carbon atom singly bonded to another atom of the compound, doubly bonded to a first oxygen atom and singly bonded to a second oxygen atom, wherein the second oxygen atom is further bonded to an atom other than hydrogen such as an atom of an organic moiety. Exemplary carboxyl-protected moieties include, but are not limited to, an ester moiety, amide moiety, N-acylurea moiety, or O-acylurea moiety.

As used herein, the term "N-acylurea moiety" is intended to mean a part of a compound including the structure

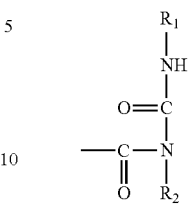

$R_1$ and $R_2$ can be the same or different and can be selected from the group consisting of hydrogen, ethyl, 3-dimethylamino propyl, cyclohexyl, 2-morpholinoethyl, isopropyl, phenyl or other organic moiety such as an optionally substituted alkyl or aryl. Furthermore, 2 of the R groups can be joined together to form a ring structure.

As used herein, the term "O-acylurea moiety" is intended to mean a part of a compound including the structure

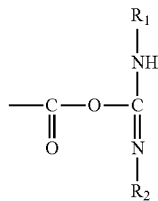

$R_1$ and $R_2$ can be the same or different and can be selected from the group consisting of hydrogen, ethyl, 3-dimethylamino propyl, cyclohexyl, 2-morpholinoethyl, isopropyl, phenyl or other organic moiety such as an optionally substituted alkyl or aryl. Furthermore, 2 of the R groups can be joined together to form a ring structure.

As used herein, the term "phosphomonoester moiety" is intended to mean a part of a compound having a phosphorus atom bound to another atom of the compound and bound to 3 different oxygen atoms. Typically, a first oxygen atom is double bonded to the phosphorus, the second and third oxygens are singly bonded to the phosphorus, and the second and third oxygen atoms are either negatively charged (O—) or bonded to a hydrogen as a hydroxyl moiety (OH). A phosphomonoester having one or more negatively charged oxygens can have any of a variety of the same or different counter ions (for example, sodium, potassium or the like). Various ionic forms of phosphomonoester can occur including, for example, the free acid, mono-anion, or di-anion. A phosphomonoester moiety can be in the form of a monophosphate or a portion of a phosphoric anhydride such as a diphosphate, triphosphate etc.

As used herein, the term "phosphoric amide" is intended to mean a part of a compound having a phosphorus atom bound to another atom of the compound, to a nitrogen atom of an organic moiety and to 2 different oxygen atoms, wherein a first oxygen atom is double bonded to the phosphorus and a second oxygen is singly bonded to the phosphorus, and the second oxygen atom is either negatively charged (O—) or bonded to a hydrogen as a hydroxyl moiety (OH).

As used herein, the term "carbodiimide compound" is intended to mean a molecule including a —N=C=N— moiety. A carbodiimide useful in the invention can have a structure

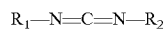

$R_1$ and $R_2$ can be the same or different and can be selected from the group consisting of hydrogen, ethyl, 3-dimethylamino propyl, cyclohexyl, 2-morpholinoethyl, isopropyl, phenyl or other organic moiety such as an optionally substituted alkyl or aryl. Furthermore, the R groups can be joined together to form a ring structure. Exemplary carbodiimide compounds include, but are not limited to, 1-ethyl-3(3-dimethylaminopropyl) carbodiimide (EDC); 1-cyclohexyl-3(2-morpholinoethyl) carbodiimide-metho-p-toluene sulfonate; (N-ethoxycarbonyl-2-ethoxy-1,2-dihydroquinoline); dicyclohexyl carbodiimide; diisopropyl carbodiimide or others known in the art such as those described in Dolinnaya et al., *Nucleic Acid Research* 19:3073-3080 (1991), which is incorporated herein by reference. In general a carbodiimide is used in the form of an acid addition salt, e.g., hydrochloride, thereof.

As used herein, the term "amine" is intended to mean a compound containing nitrogen. The compound can be an organic compound having structure $R_{3-x} NH_x$, where R is an organic moiety and $0<x<3$. Exemplary forms of these organic compounds include a primary amine (x=2), secondary amine (x=1), or tertiary amine (x=0). An amine can be neutral or positively charged.

As used herein, the term "label moiety" is intended to mean one or more atoms that can be specifically detected to indicate the presence of a substance to which the one or more atoms are attached. A label moiety can be a primary label that is directly detectable or secondary label that can be indirectly detected, for example, via interaction with a primary label. Exemplary primary labels include, without limitation, an isotopic label such as a naturally non-abundant heavy isotope or radioactive isotope, examples of which include $^{14}C$, $^{123}I$, $^{124}I$, $^{125}I$, $^{131}I$, $^{32}P$, $^{35}S$ or $^3H$; optically detectable moieties such as a chromophore, luminophore, fluorophore, quantum dot or nanoparticle; electromagnetic spin label; calorimetric agent; magnetic substance; electron-rich material such as a metal; electrochemiluminescent label such as $Ru(bpy)_3^{2+}$; moiety that can be detected based on a nuclear magnetic, paramagnetic, electrical, charge to mass, or thermal characteristic; or light scattering or plasmon resonant materials such as gold or silver particles. Fluorophores that are useful in the invention include, for example, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythrin, green fluorescent protein and its wavelength shifted variants, bodipy, fluorescent lanthanide complexes, including those of Europium and Terbium, and other fluorophores known in the art such as those described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066, each of which is hereby incorporated by reference.

Exemplary secondary labels that can be used in the invention include, without limitation, a binding moiety such as a receptor, ligand or other member of a pair of molecules having binding specificity for each other. Exemplary binding moieties having specificity for each other include, without limitation, streptavidin & biotin, avidin & biotin or an antigen & antibody such as rabbit IgG & anti-rabbit IgG. Specific affinity between two binding partners is understood to mean preferential binding of one partner to another compared to binding of the partner to other components or contaminants in the system. Depending upon the particular binding conditions used, the dissociation constants of the pair can be, for example, less than about $10^{-4}$, $10^{-5}$, $10^{-6}$, $10^{-7}$, $10^{-8}$, $10^{-9}$ $10^{-10}$, $10^{-11}$, or $10^{-12}$ $M^{-1}$. Secondary labels also include enzymes or their substrates, wherein the combination produces a detectable product, examples of which include horseradish peroxidase, alkaline phosphatase, β-galactosidase, or acetylcholinesterase each of which produce colorimetric products using color reagents that are commercially available, for example, from Sigma-Aldrich (St. Louis, Mo.) or Invitrogen (Carlsbad, Calif.).

The terms "receptor" and "ligand" are used herein for semantic clarity in identifying binding partners and are intended to be interchangeable, unless explicitly indicated to the contrary. Accordingly, the term "receptor" is intended to mean a molecule that is capable of selectively binding a ligand and the term "ligand" is intended to mean a molecule that is capable of selectively binding a receptor. The terms are intended to encompass receptors or ligands that have other functions as well. However, the terms are not intended to be limited by any other function unless indicated otherwise. For example, a receptor can be a naturally occurring polypeptide having signal transducing activity or a functional fragment thereof that exhibits selective binding to a ligand whether or not the functional fragment has signal transducing activity.

As used herein, the term "array" refers to a population of different probe molecules that are attached to one or more solid-phase substrates such that the different probe molecules can be differentiated from each other according to their relative location. An array can include different probe molecules that are each located at a different addressable location on a solid-phase substrate. Alternatively, an array can include separate solid-phase substrates each bearing a different probe molecule, wherein the different probe molecules can be identified according to the locations of the solid-phase substrates on a surface to which the solid-phase substrates are attached or according to the locations of the solid-phase substrates in a liquid such as a fluid stream.

DESCRIPTION OF PARTICULAR EMBODIMENTS

The invention provides a method of modifying a phosphomonoester moiety of a target compound. The method can include the steps of (a) providing a target compound having an electrophilic, moiety and a phosphomonoester moiety; (b) contacting the target compound with a first carbodiimide compound under conditions for preferential addition of the first carbodiimide compound to the electrophilic moiety over the phosphomonoester moiety, thereby forming an electrophile-protected target compound; and (c) contacting the electrophile-protected target compound with a second carbodiimide compound and a nucleophilic compound under conditions for addition of the nucleophilic compound to the phosphomonoester.

A target compound can have any of a variety of electrophilic moieties including, for example, an amine-reactive moiety such as a carboxylic acid moiety. Other amine-reactive moieties that may be present in a target compound include, for example, a carboxylic acid derivative such as an ester, amide, anhydride or acyl halide, or an aldehyde.

An electrophile-protected target compound can be produced by reacting an electrophilic moiety of the target compound with a nucleophilic compound having an amine, hydrazine, sulfhydril, hydroxyl or other phosphate reactive moiety.

Accordingly, in a particular embodiment, the invention provides a method of modifying a phosphomonoester moiety of a target compound. The method can include the steps of (a) providing a target compound having a carboxylic acid moiety and a phosphomonoester moiety; (b) contacting the target compound with a first carbodiimide compound under conditions for preferential addition of the first carbodiimide compound to the carboxylic acid moiety over the phosphomonoester moiety, thereby forming a carboxyl-protected target compound; and (c) contacting the carboxyl-protected target compound with a second carbodiimide compound and an amine under conditions for addition of the amine to the phosphomonoester.

The invention can be used to modify a phosphomonoester moiety of any of a variety of target compounds including, for example, a naturally occurring compound such as a nucleotide, polynucleotide, phosphorylated L-amino acid, phosphorylated protein, phosphorylated sugar, phosphorylated lipid, phosphorylated cofactor or phosphorylated metabolite. The invention can also be used to modify a phosphomonoester moiety of a synthetic target compound whether it is non-naturally occurring or a synthetic version of a naturally occurring compound. Examples include non-natural amino acids, proteins including non-natural amino acids, small molecule drug candidates, modified polynucleotides, non-natural carbohydrates or non-natural lipids. Exemplary non-natural amino acids that can have a phosphomonoester moiety include, but are not limited to, D-isomers of naturally occurring amino acids, such as D-serine, D-threonine, D-glutamic acid, D-aspartic acid or D-tyrosine; L- or D-isomers of homoserine, hydroxylated tryptophan, 3-nitro-tyrosine or other amino acids having a hydroxyl or carboxylic acid moiety. Proteins and amino acids useful in the invention can be obtained from a commercial supplier such as EMD biosciences (Darmstadt, Germany, see the Novabiochem catalog) Advanced Chemtech (Louisville, Ky.), Peptides International (Louisville, Ky.), Chem-Impex (Wood Dale, Ill.), TCI America (Portland Oreg.), or Matrix Scientific (Columbia, S.C.).

The invention is particularly useful for a target compound that is a protein (i.e. a protein target). A protein target can have one or more phosphomonoester moieties that are modified in accordance with the invention. Exemplary phosphomonoester moieties that are commonly found in proteins and that can be modified as set forth herein include, for example, the L-isomers of phosphoserine, phosphothreonine, phosphotyrosine, phosphoglutamate, phosphoaspartate or phosphohistidine. In some embodiments, one or more phosphomonoester moieties of a single type are modified in a method of the invention. For example, a protein target can have one or more phosphotyrosines as a result of phosphorylation by a tyrosine kinase. However, a protein target can have more than one type of phosphomonoester moiety, for example, as a result of phosphorylation by a kinase that phosphorylates multiple amino acids, such as a serine/threonine kinase, or as a result of phosphorylation by multiple kinases. Various phosphomonoester moieties of proteins have been exemplified above with respect to the activity of kinase enzymes; however it will be understood that a protein can include a phosphomonoester moiety that was added by an in vitro synthetic chemical method.

A target compound can be obtained from a natural source or synthetic source. Exemplary natural sources include, but are not limited to a cell, bodily fluid, tissue or other source such as those set forth in further detail below. Those skilled in the art will know or be able to readily determine methods for isolating a target compound from a synthetic or natural source using methods known in the art. For example, a protein target can be isolated using methods such as those described in Scopes, *Protein Purification* 3$^{rd}$ Ed., Springer Verlag, New York (1994) or Coligan et al., *Current protocols in Protein Science*, John Wiley and Sons, Baltimore, Md. (2000), each of which is hereby incorporated by reference. In particular embodiments of the invention, a crude cell lysate containing a collection of target compounds, such as proteins, can be directly detected in a method of the invention without further isolation. Alternatively, one or more target compounds can be further isolated from at least one other cellular component prior to use in a method described herein.

Any of a variety of methods known in the art can be used for in vitro production of a synthetic target compound. For example, a protein target can be synthesized using methods described in Goodman et al. (Eds.), *Synthesis of Peptides and Peptidomimetics*, Vol. E22a. Georg Thieme Verlag, Stuttgart (2002), which is hereby incorporated by reference. Protein targets, whether obtained from a synthetic or natural source can be isolated using known methods including, for example, liquid phase extraction, precipitation, solid-phase extraction, chromatography, centrifugation or the like. Such methods are described, for example, in Scopes, supra (1994) or Coligan et al., supra (2000).

A protein target used in accordance with the invention can be a fragment of a larger protein. Thus, a portion of a larger protein that is believed to have a phosphomonoester moiety or that is believed to be capable of being phosphorylated can be obtained and used. A larger protein can be fragmented to obtain a desired protein target, for example, by using a protease or chemical cleavage method. Any of a variety of proteases or chemical cleavage methods known in the art can be used including, for example, those described in Coligan et al., supra (2000) or Barrett et al., *Handbook of Proteolytic Enzymes*, Elsevier, Amsterdam, The Netherlands (2004), each of which is hereby incorporated by reference. If desired, a fragment to be used as a protein target can be isolated from at least one other fragment of the larger protein. However, fragments need not be isolated and can be used in a mixture if desired.

Fragmentation can be carried out prior to, during or after reaction of the protein target with a carbodiimide compound for protection of an electrophile. Furthermore, fragmentation can be carried out prior to, during or after reaction of the protein target with a carbodiimide compound and a nucleophile for modification of a phosphomonoester moiety. In embodiments where the protein target is treated with a kinase, phosphatase or other agent such treatment can be carried out, prior to, during or after fragmentation. A protein target can be attached to a solid-phase substrate, for example, via linkage to a phosphate moiety or other moiety, during fragmentation or fragmentation can occur in solution-phase.

A protein target used in a method of the invention will have a primary structure consisting of its sequence of amino acids. Typically, protein targets will also have one or more secondary structure elements such as an alpha helix, or beta sheet. A sufficient number of amino acids can also be present in a protein to allow formation of tertiary structure, also referred to as a protein fold. Furthermore, a target protein can include two or more amino acid chains that are associated according to a quaternary structure. A protein target used in the invention can be in a native state with respect to its primary, secondary, tertiary, and/or quaternary structure. However, if desired a target protein can be treated such that it loses native structure at one or more of the 4 levels. For example, denaturation can be carried out to alter quaternary, tertiary or even secondary structure by the addition of reagents such as urea, guanidinium salts, detergents, organic solvents; heating, mechanical disruption or other known methods.

Denaturation typically leads to loss of function for the protein target, thereby forming an inactivated protein target. A protein target can be denatured or otherwise inactivated, for one or more reactions utilized in a method of the invention. For example, an inactivated protein target can be treated with carbodiimide and a nucleophilic compound for modification of a phosphomonoester moiety of the protein target. If desired, a target protein can also be in an inactivated state when electrophilic moieties such as carboxylic acids are protected by a carbodiimide compound. Inactivated protein targets can also be treated with one or more kinases or phosphatases in a method of the invention. Such inactivation, for example, when removing tertiary or quaternary structure, can provide the advantage of exposing a phosphomonoester moiety and/or carboxylic acid moiety that is sterically blocked from a desired reaction when in the protein target is in a native conformation. Alternatively, use of a protein target in a native conformation is desirable for some embodiments of the invention, for example, when preferential modification of surface exposed moieties of the native protein target is desired or when reaction of internal amino acids of a native protein target is to be avoided or reduced.

In particular embodiments, a target compound can be attached to a moiety that allows detection or fractionation of the target compound. For example, a target compound can be attached to a label moiety such as one or more of the primary labels or secondary labels described herein. A particularly useful label is a nucleic acid moiety having a sequence that can be used to identify the target compound to which it is attached. As demonstrated in Example I, the use of different nucleic acid labels each having a different nucleotide sequence and each attached to a particular target compound in a plurality of different target compounds, can allow the target compounds to be distinguished according to their location on an array of complementary nucleic acid probes. Similar array based detection of different target compounds can be used with other label moieties as well.

A target protein can be attached to a nucleic acid moiety in any of a variety of configurations. In particular embodiments, a protein target is attached to a nucleic acid moiety in a linear arrangement such that the nucleotide at the 3' or 5' end of the nucleic acid moiety is attached to the carboxy terminus or amino terminus of the protein target. As described in Example I, attachment of the 3' end of a nucleic acid moiety to the amino terminus of a protein moiety provides a useful configuration. Alternatively, the protein and nucleic acid can be attached such that an internal amino acid of the protein target is attached to the nucleic acid moiety and/or an internal nucleotide of the sequence of the nucleic acid moiety is attached to the protein target. Typically, the nucleic acid moiety, when used as a label, will not have a phosphomonoester moiety.

Attachment of a protein target and nucleic acid moiety is typically mediated by at least one covalent bond. An attaching bond can be made to any desired portion of a protein target including, without limitation, a backbone carbon, nitrogen or oxygen or a sidechain ("R") group. Similarly, a bond can be made to any desired portion of the nucleic acid moiety including, but not limited to, the backbone or base. In the exemplary case where DNA or RNA is used, an attaching bond can be made to the phosphodiester backbone, the sugar moiety or the base. If DNA or RNA analogs, such as those set forth above, are used then a covalent bond used for attachment can be made to known structural moieties therein. Attachment of a PNA-based nucleic acid moiety to a protein moiety is particularly convenient since both moieties contain a similar backbone structure. More specifically, the two moieties can be attached via a peptide bond between the terminal alpha carbonyl of one moiety and terminal alpha amino of the other moiety. PNA or peptide-PNA chimaeras can be synthesized using methods known in the art as described, for example, in U.S. Pat. No. 6,713,602 or Nielsen et al. *Science* 254:1497-1500 (1991), each of which is hereby incorporated by reference.

An exemplary method for attaching a protein moiety to a DNA moiety is coupling a benzaldehyde residue on the DNA moiety with an aminooxyacetic on the amino terminus of the protein to form an oxime bond. Further, exemplary methods for attaching a DNA moiety to a protein moiety include coupling a benzaldehyde residue on the DNA with a hydrazine on the amino terminus of the protein to moiety to form a hydrazone bond, and other methods described in U.S. Ser. No. 11/090,094, filed on Mar. 25, 2005, Zubin et al., *Russian Chemical Reviews* 71:239-264 (2002) or Tung et al., *Bioconjugate Chemistry* 11:605-618 (2000), each of which is hereby incorporated by reference.

Attachment between a target compound and label moiety can be mediated by covalent bonds, such as those exemplified above. Non-covalent interactions can also mediate attachment between moieties. For example, each moiety can include a partner capable of forming a receptor-ligand complex such as avidin & biotin or other pairs set forth elsewhere herein or known in the art.

A target compound used in a method of the invention can be in solution or attached to a solid-phase surface. Furthermore, the target compound can occur in solution-phase or solid-phase for different steps of a method set forth herein. Exemplary embodiments are described in Example I, wherein a target protein-DNA conjugate having a phosphorylated amino acid is contacted with a carbodiimide compound and a dye having an amine moiety in solution phase. As further demonstrated in Example I, the dye-modified target can subsequently be attached to a solid-phase substrate via interaction of the DNA portion of the conjugate with a complementary DNA probe on the solid-phase substrate. Several of the embodiments described in Example I also include pre-treatment of the DNA-protein conjugate with a carbodiimide compound in solution to form a carboxyl-protected DNA-protein conjugate.

In particular embodiments, a target compound that is attached to a solid-phase substrate can be contacted with a carbodiimide compound and an amine under conditions for addition of the amine to one or more phosphomonoesters of the target compound. If desired, the target compound can be pre-treated while attached to a solid-phase substrate, for example, by contacting the solid-phase-bound target compound to a carbodiimide compound under conditions for preferential addition of the carbodiimide compound to a carboxylic acid moiety of the compound over the phosphomonoester moiety of the compound, thereby forming a carboxyl-protected target compound.

In embodiments, including attachment of a target compound or other agent to a solid-phase substrate, particularly useful solid-phase substrates include, for example, magnetic beads which can be easily introduced to a reaction mixture and easily removed with a magnet. Other known affinity chromatography substrates can be used as well. Known methods can be used to attach a nucleic acid or protein moiety to a solid support including, for example, those described in U.S. patent application Ser. Nos. 10/651,568 or 10/739,959, WO 01/41918, or WO 04/001646, each of which is hereby incorporated by reference. A solid support can be selected, for example, from those materials described below with respect to detection arrays.

A plurality of target compounds can be used in a method of the invention. Example I demonstrates, evaluation of pools having 6, 96, 100, or 194 target compounds. Further examples of pool sizes that can be used in the invention include, but are not limited to, those having at least about 5, 10, 50, 100, 500, $1 \times 10^3$, $1 \times 10^4$, $1 \times 10^5$, $1 \times 10^6$ or more target compounds. The target compounds in a pool can be treated simultaneously or sequentially in a method of the invention, such that all or a subset of the target compounds are modified to have a protected electrophile moiety or a nucleophile-modified phosphate moiety or both. Furthermore, a method can be used in a multiplex format wherein a pool of several target compounds is treated with a pool of several different agents such as a pool of kinases, phosphatases, or inhibitors. The pool of agents can include, for example, at least about 5, 10, 50, 100, 500, $1 \times 10^3$, $1 \times 10^4$, $1 \times 10^5$, $1 \times 10^6$ or more different agents. A multiplex reaction can include any combination of these exemplary numbers of target compounds and other agents. Methods including use of such other agents are set forth in further detail below and demonstrated in Example I.

Multiple target compounds or other agents used in accordance with the invention can be attached to one or more solid-phase substrates. Other agents include, without limitation, one or more kinases, phosphatases, receptors for secondary labels or other components of the methods set forth herein. One or more solid-phase substrates used in the invention can be in the form of an array. In particular embodiments, target compounds or other agents can be attached to particles that are arrayed or otherwise spatially distinguished. Exemplary particles include microspheres or beads. It will be understood that particles such as microspheres or beads can be spherical or approximately spherical but need not be perfectly spherical. Rather, solid-phase particles having other shapes including, but not limited to, cylinders, disks, plates, chips, slivers or irregular shapes can be used. In addition, particles used in the invention can be porous having internal surfaces, thus increasing the surface area available for attachment or detection of target compounds or other agents. Particle sizes can range, for example, from nanometers such as about 100 nm beads, to millimeters, such as about 1 mm beads, with particles of intermediate size such as at most about 0.2 micron, 0.5 micron, 5 micron or 200 microns being useful.

The composition of particles useful in the invention can vary depending, for example, on the application of the invention or the method of synthesis. Typically, useful particles consist of a substantially non-compressible or inelastic material compared to a biological cell, examples of which include plastics, ceramics, glass, polystyrene, methylstyrene, acrylic polymers, paramagnetic materials, thoria sol, carbon graphite, titanium dioxide, latex, Teflon™, cross-linked dextrans such as Sepharose™, cellulose, or nylon. However, if desired a biological cell or similarly compressible particle such as a cross-linked micelle can be used as a solid-phase support in the invention. Other suitable particle compositions include, but are not limited to, those used in peptide (protein), nucleic acid and organic moiety synthesis or others described, for example, in *Microsphere Detection Guide*, Bangs Laboratories, Fishers Ind., which is hereby incorporated by reference.

Exemplary bead-based arrays that can be used in the invention include, without limitation, those in which beads are associated with a solid support, examples of which are described in U.S. Pat. No. 6,355,431 B1, US 2002/0102578 and PCT Publication No. WO 00/63437, each of which is hereby incorporated by reference. A particularly useful solid support is a fiber optic bundle as described, for example, in U.S. Pat. No. 6,200,737; WO 98/40726; or WO 98/50782, each of which is hereby incorporated by reference. Beads can be located at discrete locations, such as wells, on a solid-phase support, whereby each location accommodates a single bead. Alternatively, each discrete location can include a plurality of beads as described, for example, in US Pat. App. Pub. Nos. US 2004/0263923, US 2004/0233485, US 2004/0132205, or US 2004/0125424, each of which is hereby incorporated by reference. It will be understood that the sites of an array of the invention need not be discrete sites. For example, it is possible to use a uniform surface of adhesive or chemical functionalities that allows the attachment of particles at any position.

Beads or other particles can be loaded onto array supports using methods known in the art such as those described, for example, in U.S. Pat. No. 6,355,431, which is hereby incorporated by reference. In some embodiments, particles can be randomly deposited on a solid-phase substrate. In embodiments where the placement of particles is random, a coding or decoding system can be used to localize and/or identify the particles at each location in the array, thereby locating the target compound or other agent attached to the particle. This can be done in any of a variety of ways, for example, as described in U.S. Pat. No. 6,355,431 or WO 03/002979, each of which is hereby incorporated by reference. A further coding system that is useful in the invention is the use of diffraction gratings as described, for example, in US Pat. App. Nos. US 2004/0263923, US 2004/0233485, US 2004/0132205, or US 2004/0125424, each of which is hereby incorporated by reference. Alternatively, particles can be attached to a support in a non-random or ordered process.

An array of beads useful in the invention can also be in a fluid format such as a fluid stream of a flow cytometer or similar device. Exemplary formats that can be used in the invention to distinguish beads in a fluid sample using microfluidic devices are described, for example, in U.S. Pat. No. 6,524,793, which is hereby incorporated by reference. Commercially available fluid formats for distinguishing particles such as beads include, for example, those used in xMAP™ technologies from Luminex or MPSS™ methods from Lynx Therapeutics.

Any of a variety of other arrays known in the art can be used in the present invention for attachment of target compounds or other agents. Commercially available microarrays that can be used in the invention include, for example, an Affymetrix®GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies. Other microarrays that can be used in the invention include, without limitation, those described in Butte, *Nature Reviews Drug Discov.* 1:951-60 (2002) or U.S. Pat. Nos. 5,429,807; 5,436,327; 5,561,071; 5,583,211; 5,658,734; 5,837,858; 5,919,523; 6,287,768; 6,287,776; 6,288,220; 6,297,006; 6,291,193; and 6,514,751; and WO 93/17126; WO 95/35505, each of which is hereby incorporated by reference.

The surface of a solid-phase support can include a plurality of individual arrays that are physically separated from each other by any of a variety of partitions. In particular embodiments, physical separation can be due to the presence of assay wells, such as in a microtiter plate. Such a composite array (or array of arrays) can allow parallel processing of multiple samples in a method of the invention. For example, multiple samples each having a plurality of different target compounds and/or other agents can be treated in parallel using a composite array for multiplex detection of the phosphorylation states of the target compounds on each array. Exemplary composite arrays that can be used in the invention are described in U.S. Pat. No. 6,429,027; WO 02/00336 and U.S. Pat. App. Pub. No. 2002/0102578, each of which is hereby incorporated by reference.

A solid-phase support used in an array of the invention can include any material that is capable of being attached to a desired target compound or other agent. Useful supports include, but are not limited to, glass; modified glass; functionalized glass; plastics such as acrylics, polystyrene and copolymers of styrene and other materials, polypropylene, polyethylene, polybutylene, polyurethanes, Teflon, or the like; polysaccharides; nylon; nitrocellulose; resins; silica; silica-based materials such as silicon or modified silicon; carbon; metal; inorganic glass; optical fiber bundles, or any of a variety of other polymers. Useful supports include those that allow optical detection, for example, by being translucent to energy of a desired detection wavelength and/or by themselves not appreciably fluorescent at particular detection wavelengths.

In particular embodiments, it is desired to detect phosphorylation state, kinase activity or phosphatase activity using assays having redundancy with regard to a particular target compound. Redundancy can be particularly useful for increasing confidence levels or determining statistical validity for measurements such as kinetic or thermodynamic properties of kinase or phosphatase activity including, for example, binding constants, maximum velocity, catalytic rate constant or others determined using methods set forth in further detail below and in Segel, *Enzyme Kinetics: Behavior and Analysis of Rapid Equilibrium and Steady-State Enzyme Systems*, Wiley, John & Sons, Incorporated (1994), which is hereby incorporated by reference. Several other non-limiting advantages of such redundancy, include the ability to make quantitative estimates of confidence about collected data. Also redundancy can provide substantial increases in sensitivity due to the ability to sum signals from different target compounds. A variety of statistical mathematical analyses can be done for analysis of large data sets. Exemplary analyses include, but are not limited to, baseline adjustment, averaging, standard deviation analysis, distribution and cluster analysis, confidence interval analysis, mean testing, or the like, as described in texts such as Freund and Walpole, *Mathematical Statistics*, Prentice Hall Inc., New Jersey (1980), which is hereby incorporated by reference. Methods for making and using redundant arrays are described, for example, in U.S. Pat. No. 6,355,431 and WO 00/60332, each of which is hereby incorporated by reference.

A method of the invention can, optionally, include a step of contacting a target compound with a carbodiimide compound under conditions for preferential addition of the carbodiimide compound to an electrophile moiety, such as a carboxylic acid moiety, of the target compound, thereby forming an electrophile-protected target compound such as a carboxyl-protected target compound. Preferential addition of a reagent to a first moiety over a second moiety in a reaction can result in exclusive addition of the reagent to the first moiety. However, exclusive addition to a particular moiety is not necessarily required. Thus, preferential addition can result in a product having a larger proportion of the reagent attached to the first moiety than the amount of reagent attached to the second moiety. For example, in embodiments where phosphomonoester moieties of a target compound are to be modified, a population of target compounds can be pre-treated under conditions for preferential addition of carbodiimide compound to electrophilic moieties of the target compounds, wherein a lesser amount of carbodiimide compound is added to the phosphomonoester moieties, so long as a sufficient free phosphomonoester moieties are available for subsequent modification.

An example of an electrophilic moiety that can be protected in a method of the invention is a carboxylic acid moiety. A carbodiimide compound can be preferentially added to a carboxylic acid moiety over a phosphomonoester moiety at low pH. An example of the use of low pH for preferential addition of a carbodiimide compound to a carboxylic acid moiety is provided in Example I where pH 4.5 is used. The pH used in a method of the invention can be at most about 3, 4, 5, 6, 7 or higher and/or at least about 6, 5, 4, 3, 2 or lower. In particular embodiments, the preferential addition of a carbodiimide compound to a carboxylic acid can be carried out at a pH in the range of 2.0 to 7.5.

The pH can be chosen to suit a particular target compound. For example, a protein target having acid-stable phospho-amino acids, such as phosphoserine, phosphothreonine or phosphotyrosine, can be subjected to low pH for an extended period of time. Thus, the methods can be used to Modify a phosphomonoester moiety of an acid-stable target compound such as one or more acid-stable phospho-amino acids of a protein target. Acid-labile target compounds can also be used under appropriate conditions. For example, treatment of a target protein having an acid-labile phospho-amino acid, such as phosphohistidine, in order to protect a carboxylic acid moiety, can be carried out at higher pH and/or for shorter reaction times compared to the conditions used for a target protein having an acid-stable phosphomonoester moiety.

Figure 1:
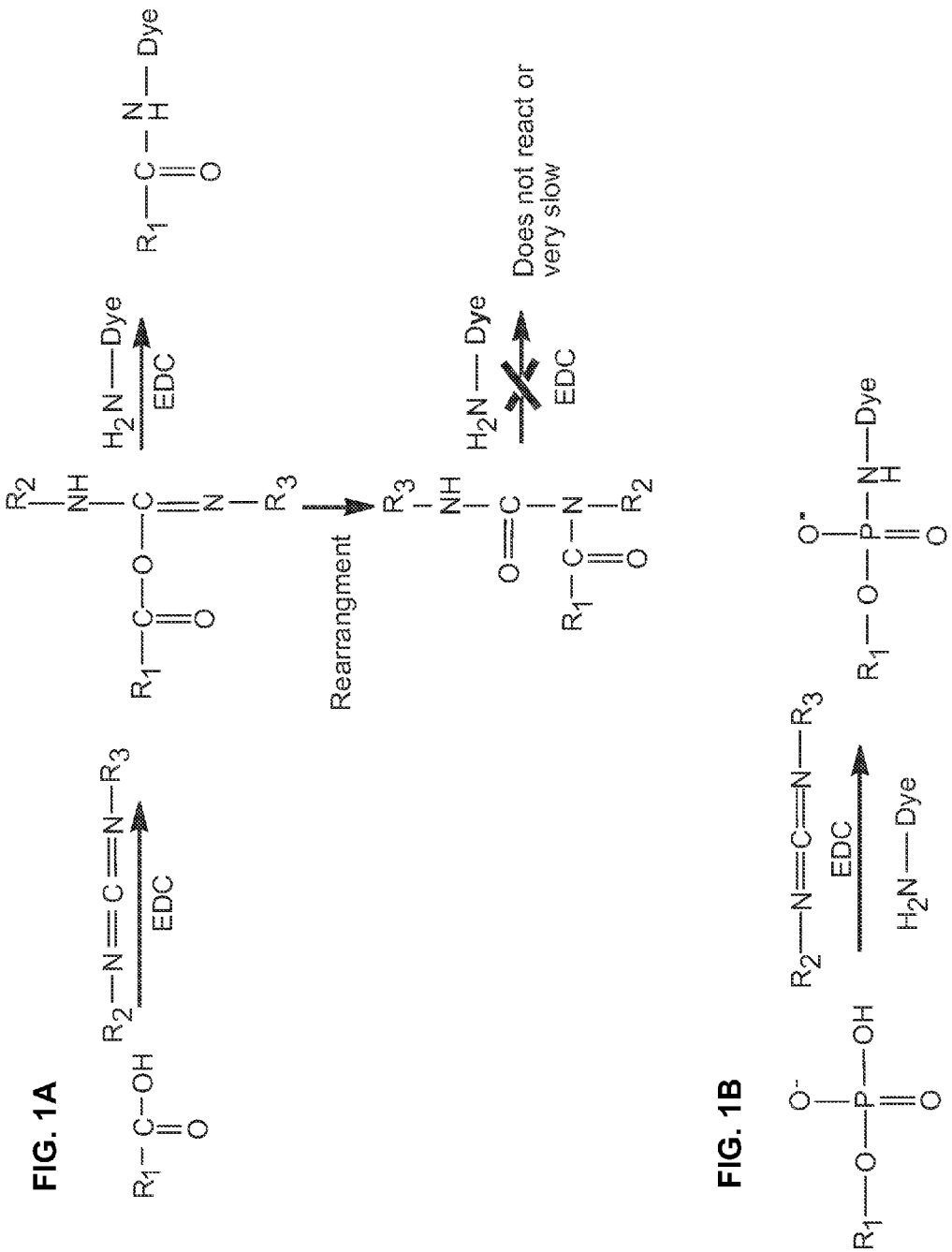
FIG. 1 shows reactions for derivatization of a carbonyl moiety with an O-acylurea or N-acylurea moiety (reaction A)

A possible mechanism for protecting a carboxyl moiety with a carbodiimide compound is provided in FIG. 1. This mechanism is provided for purposes of illustration and is not necessarily intended to limit the invention set forth herein. In this regard, it will be understood that a protected carbonyl made or used in accordance with this disclosure can have a structure other than those conjectured in FIG. 1. Nevertheless, as shown in FIG. 1, reaction of a carbodiimide compound with a carboxylic acid is believed to produce an O-acylurea, which is subsequently rearranged to form an N-acylurea. Accordingly, reaction of a carbodiimide compound with a carboxylic acid moiety can be allowed to proceed under conditions for formation of either an O-acyl moiety or an N-acylurea moiety. As described in Example I, reaction at low pH for 90 minutes was sufficient to protect carboxyl moieties of protein targets, presumably by formation of N-acylurea moieties. Any reaction time sufficient to protect a carboxyl moiety, for example, by formation of an N-acylurea moiety can be used.

A method of the invention can, optionally, include a step of contacting a target compound with a carbodiimide compound and a nucleophilic compound, such as an amine, under conditions for addition of the nucleophilic compound to a phosphomonoester of the target compound. The target compound can be, but need not be, an electrophile-protected compound such as a carboxyl-protected target compound.

In embodiments wherein a target compound is contacted with a first carbodiimide to form an electrophile-protected target compound and the electrophile-protected target compound is contacted with a second carbodiimide under conditions for addition of a nucleophile to the electrophile-protected target compound, the first and second carbodiimide compounds can be the same molecular species. An advantage of the methods as carried out in such embodiments is that the target compound need not be isolated from other reaction components between the reaction for electrophile-protection and the reaction for nucleophilic addition (i.e. the method can be carried out in a one-pot reaction). Thus, not only can the same species of carbodiimide compound be used to activate both reactions, but both can be added to the same reaction vessel. The first and second carbodiimide compounds can be added to the vessel simultaneously or sequentially, as desired. For example, an amount of carbodiimide sufficient to activate both reactions can be initially added to a reaction vessel such that excess carbodiimide present after completion of the electrophile-protection reaction is available for the nucleophilic addition reaction. In this case, a subpopulation of the carbodiimide compounds can contact the electrophile to produce the electrophile-protected target compound and the excess carbodiimide from this reaction can then contact the phosphomonoester moiety for activation of the nucleophilic addition reaction. Continuing with the example of a one pot reaction, the nucleophilic addition reaction can be initiated by addition of the nucleophile to the reaction vessel. The advantages set forth above can be extended to any of a variety of reaction vessels including, without limitation, a tube, multi-well plate, solid-phase surface, array or flow cell.

If desired, different molecular species of carbodiimide can be used for one or more reactions that occur in a method of the invention. Different molecular species of carbodiimide compound can be used, for example, in cases where different species are known or believed to have different efficiencies for each reaction. Again, the different molecular species of carbodiimide can be added to a reaction vessel simultaneously or sequentially.

Any of a variety of carbodiimide compounds capable of modifying a carboxylic acid moiety or activating phosphomonoester moiety for nucleophilic addition or both can be used in the invention. Exemplary, carbodiimide compounds include, but are not limited to, 1-ethyl-3(3-dimethylaminopropyl) carbodiimide (EDC); 1-cyclohexyl-3(2-morpholinoethyl) carbodiimide-metho-p-toluene sulfonate; (N-ethoxycarbonyl-2-ethoxy-1,2-dihydroquinoline); dicyclohexyl carbodiimide; diisopropyl carbodiimide or others known in the art such as those described in Dolinnaya et al., *Nucleic Acid Research* 19:3073-3080 (1991), which is incorporated herein by reference. By way of example, use of EDC for modification of carboxylic acid moieties and activation of phosphomonoester moieties is set forth in Example I. The above carbodiimides or others known in the art can be used to activate other electrophilic moieties in a method of the invention and can be selected for desired reactivity or other characteristics according to the particular application of the method.

Addition of a nucleophile to a carbodiimide-activated phosphomonoester of a target compound using a method set forth herein can allow any of a variety of phosphomonoester-specific modifications of the target compound. In particular embodiments, the modification can be attachment to a solid-phase substrate. For example, a nucleophilic compound, such as an amine, that is reacted with a target compound can be attached to a solid-phase substrate. Accordingly, following activation of a phosphomonoester moiety of the target compound with a carbodiimide compound and addition of the solid-phase bound amine, the target compound will be attached to the solid-phase via the phosphate moiety. The solid-phase substrate can be any of those set forth above in regard to attachment of a target compound including, for example, a particle or array solid-phase substrate.

A nucleophilic compound can be attached to a solid-phase substrate by reaction with any of a variety of linkers having a phosphomonoester reactive moiety. Solid-phase substrates having phosphomonoester reactive moieties can be obtained from commercial suppliers such as Bangs Laboratories (Fishers, Ind.), Pierce Chemicals (Rockford, Ill.) or Sigma-Aldrich (St. Louis, Mo.). The linkage between a solid-phase and phosphomonoester moiety of a target compound can be polymeric, for example, including a polypeptide or polynucleotide sequence, hydrophobic or hydrophilic. A linker can further include a cleavable moiety, examples of which include a moiety, such as ethylene glycol, that is cleavable by hydroxylamine; a moiety, such as a sulfone, that is cleavable by base; a moiety, such as a disulfide, that is cleavable by reducing agent such as a thiol; or a moiety, such as tartarate, that is cleavable by an oxidizing agent such as periodate. Other exemplary attachments include products of a reaction of a crosslinking agent, such as those set forth below, with a surface having a moiety that is reactive toward the crosslinking agent.

A method of the invention can be used to add a reactive moiety to a target compound. For example, a nucleophilic compound can be a crosslinking agent having a first reactive moiety that is reactive with phosphomonoester and a second reactive moiety. A particularly useful cross-linking agent is a heterobifunctional crosslinking agent in which the first and second reactive moieties are different species. Typically, the second reactive moiety will be inert to activation with carbodiimide and reaction with phosphomonoester. However, a crosslinking agent in which both moieties are reactive toward phosphomonoester, such as a homobifunctional crosslinking agent, can be used. Use of a crosslinking agent in which both moieties are reactive toward phosphomonoester can be used to crosslink two phosphate moieties. Alternatively or additionally, one of the moieties can have a protecting group that can be removed following nucleophilic addition of the crosslinking agent to a phosphate moiety of a target compound. Furthermore, a crosslinking agent can include a cleavable linker such as those set forth above.

Examples of phosphomonoester reactive moieties that can be included in a crosslinking agent include, but are not limited to, an amine, hydrazine, sulfhydril or hydroxyl. The second moiety of a crosslinking agent can be reactive to phosphomonoester and/or other moieties. Examples include, but are not limited to, a second moiety that is reactive toward carboxylic acid, such as an amine moiety; a second moiety that is photoreactive such as a nitrophenyl azide or hydroxyphenyl azide moiety; a second moiety that is reactive toward an amine moiety such as a carboxylic acid, NHS-ester or imidoester; or a second moiety that is reactive toward sulfhydril, such as a maleimide, pyridyldisulfide, pyridyldithio, bromoacytal or iodoacytal. Another example of a useful linker is cysteamine, which has an amino moiety that can be added to a phosphomonoester moiety as described herein, and an internal disulfide that can be subsequently reduced to generate a reactive free sulfhydril moiety. Crosslinking agents can be obtained from commercial suppliers such as Pierce Chemicals (Rockford, Ill.) or Sigma-Aldrich (St. Louis, Mo.).

In particular embodiments, a label moiety can be attached to the phosphomonoester in a method of the invention. For example, a nucleophile, such as an amine, that is added to a carbodiimide-activated phosphomonoester can include a label moiety. Modification to add a label to a phosphorylated target compound is demonstrated in Example I. Exemplary label moieties include, but are not limited to primary and secondary labels set forth previously herein. Detection of the label moiety can be used to determine presence of a phosphomonoester moiety in a target compound.

Accordingly, the invention further provides a method of detecting a phosphomonoester moiety of a target compound. The method can include the steps of (a) providing a target compound having an electrophilic moiety, such as a carboxylic acid moiety, and a phosphomonoester moiety; (b) contacting the target compound with a first carbodiimide compound under conditions for preferential addition of the first carbodiimide compound to the electrophilic moiety over the phosphomonoester moiety, thereby forming an electrophile-protected target compound; (c) contacting the electrophile-protected target compound with a second carbodiimide compound and a nucleophilic compound, such as an amine, under conditions for addition of the nucleophilic compound to the phosphomonoester moiety, thereby forming a nucleophile-modified phosphate moiety; and (d) detecting the nucleophile-modified phosphate moiety.

A nucleophilic compound that is added to a phosphate moiety can be detected due to the presence of a label moiety. Useful properties of a label moiety include, those that can be used to distinguish different target compounds alone, or in combination with other methods, such as attachment of the target compounds to solid-phase supports. Exemplary properties upon which detection can be based include, but are not limited to, mass, electrical conductivity, energy absorbance, fluorescence, magnetism, luminescence or the like.

Detection of fluorescence can be carried out by irradiating a target compound or label moiety with an excitatory wavelength of radiation and detecting emitted radiation by methods known in the art and described for example in Lakowicz, *Principles of Fluorescence Spectroscopy*, 2nd Ed., Plenum Press New York (1999), which is hereby incorporated by reference. A fluorophore can be detected based on any of a variety of fluorescence phenomena including, for example, emission, excitation, fluorescence resonance energy transfer (FRET) intensity, quenching, anisotropy or lifetime at one or more wavelengths.

Other detection techniques that can be used to detect a target compound include, for example, mass spectrometry which can be used to perceive a molecule or complex based on its mass; surface plasmon resonance which can be used to perceive a molecule or complex based on binding or dissociation from a surface; absorbance spectroscopy which can be used to perceive a molecule or complex based on the wavelength of the energy it absorbs; calorimetry which can be used to perceive a molecule or complex based on changes in temperature of its environment upon binding or dissociation; electrical conductance or impedance which can be used to perceive a molecule or complex based on changes in its electrical properties or in the electrical properties of its environment; magnetic resonance which can be used to perceive a molecule or complex based on presence of magnetic nuclei; or other known analytic spectroscopic or chromatographic techniques.

A label moiety can impart a target compound with a characteristic that allows its separation from other components of a sample. For example, the nucleophilic compound can include a ligand that is useful for affinity chromatography or solid-phase extraction of a target compound using a solid-phase having a receptor for the ligand. Alternatively or additionally, the label moiety can be used to track the modified target compound in a separation method including, for example, a chromatographic separation such as reverse-phase, normal phase, ion exchange, or size exclusion chromatography; extraction, such as solid-phase or liquid-liquid phase extraction; precipitation; gel electrophoresis; capillary electrophoresis; differential centrifugation; flow cytometry, or mass spectroscopy.

A method of the invention can further include a step of identifying the type of amino acid that is attached to a phosphomonoester moiety of a protein. The type of amino acid can be, for example, a serine, threonine, tyrosine, histidine, glutamic acid or aspartic acid. The type of amino acid can be identified based on the known sequence of the protein. For example, in the case of a short protein, such as a fragment from a larger protein, wherein the fragment has only a single amino acid that is capable of being phosphorylated under the conditions tested, the identity of the modified phosphate can be inferred from the composition and/or sequence of the fragment. Alternatively, a phospho-amino acid can be identified using an analytical method including, for example, a chromatographic technique such as reverse-phase HPLC or thin layer chromatography or a spectroscopic technique such as mass spectroscopy or nuclear magnetic resonance spectroscopy. Additionally, amino acid analyzers available from commercial sources can be used such as the Perkin Elmer Applied Biosystems Model 140C PTH Amino Acid Analyzer. Such methods can be carried out on an intact protein, or following fragmentation of the protein, for example, via chemical methods such as acid-hydrolysis and/or base hydrolysis or via enzymatic methods such as protease hydrolysis.

Furthermore, the location of the phosphorylated amino acid in the primary sequence of the protein can be determined in a method of the invention. The location can be inferred from the known sequence of the protein, for example, in combination with one or more analytical technique for identifying the type of amino acids present in a protein, such as those set forth above. If desired a protein sequencing method can be used such as a method based on Edman degradation and related chemistry. Protein sequencing instruments available from commercial sources can be used such as the Perkin Elmer Applied Biosystems Model 494 Procise protein/peptide sequencer or the Perkin Elmer QSTAR hybrid LC/MS/MS mass spectrometer.

A method of the invention can include a step of contacting a target compound with a kinase under conditions for adding a phosphate moiety to the target compound. For example, a protein target can be contacted with a protein kinase prior to treating the protein target with a carbodiimide and amine. Thus, addition of the amine can be detected as an indication of activity of the kinase toward the protein target. Any of a variety of known kinases can be used including, for example, a protein kinase (i.e. a kinase that adds a phosphate to a protein substrate), adenylate kinase, creatine kinase, pyruvate kinase, hexokinase, nucleotide diphosphate kinase or thymidine kinase. Exemplary protein kinases that are useful in the invention include, but are not limited to, a serine/threonine kinase, tyrosine kinase, histidine kinase, or aspartic acid/glutamic acid kinase. A kinase useful in the invention can be from either a prokaryote or eukaryote, including either a plant or animal.

A kinase can belong to any of the following families of proteins: cyclic nucleotide regulated protein kinase (PKA & PKG) family; diacylglycerol-activated/phospholipid-dependent protein kinase C (PKC) family; kinases that phosphorylate G protein-coupled receptors family; budding yeast AGC-related protein kinase family; kinases that phosphorylate ribosomal protein S6 family; budding yeast DBF2/20 family; flowering plant PVPK1 protein kinase homolog family;

kinases regulated by Ca2+/CaM and close relatives family; KIN1/SNF1/Nim1 family; cyclin-dependent kinases (CDKs) and close relatives family; ERK (MAP) kinase family; glycogen synthase kinase 3 (GSK3) family; casein kinase II family; Clk family; Src family; Tec/Atk family; Csk family; Fes (Fps) family; Abl family; Syk/ZAP70 family; Tyk2/Jak1 family; Ack family; focal adhesion kinase (Fak) family; epidermal growth factor receptor family; Eph/Elk/Eck receptor family; Axl family; Tie/Tek family; platelet-derived growth factor receptor family; fibroblast growth factor receptor family; insulin receptor family; LTK/ALK family; Ros/Sevenless family; Trk/Ror family; DDR/TKT family; hepatocyte growth factor receptor family, nematode Kin15/16 family; Polo family; MEK/STE7 family; PAK/STE20 family; MEKK/STE11 family; NimA family; wee1/mik1 family; kinases involved in transcriptional control family; Raf family; activin/TGFb receptor family; flowering plant putative receptor kinases and close relatives family; PSK/PTK "mixed lineage" leucine zipper domain family; casein kinase I family; and PKN prokaryotic protein kinase family.

Other known kinases that can be used include, for example, those set forth in Manning et al., *Science* 298:1912-1934 (2002); The protein kinase resource web page (kinasenet.org, administered by The San Diego Supercomputer Center and The University of California San Diego, with funds from the National Science Foundation), each of which is hereby incorporated by reference. Variants of known kinases can also be used including, for example, those known or suspected of being associated with a disease or condition, such as the kinase variants set forth at the KinMutBase (see Ortutay et al., *Hum Mutat.* 25:435-42 (2005)), which is hereby incorporated by reference.

A method of the invention can include a step of contacting a phosphorylated target compound with a phosphatase under conditions for removing a phosphate moiety from the target compound. For example, a phospho-protein target can be contacted with a phosphatase prior to treating the protein target with a carbodiimide and amine. Thus, inability of the amine to add to the target protein can be detected as an indication of activity of the phosphatase toward the phospho-protein target. The inability of the amine to add to the protein can be determined, for example, by comparison of the amount of amine on the phosphatase treated phospho-protein target to the amount of amine on the same species of phospho-protein target that has not been treated with the phosphatase. Any of a variety of known phosphatases can be used including, for example, a tyrosine phosphatase (PTP), serine/threonine phosphatase, metalloenzyme phosphatase, non-metalloenzyme phosphatase, cysteine phosphatase, dual-specificity phosphatase (DSPs); Cdc25 phosphatase, myotubularin-related phosphatase, low molecular weight phosphatase, inositol 4-phosphatase or Sac1-domain phosphatase. Other known phosphatases that can be used include, for example, those set forth in Andersen et al., *Mol. Cell. Biol.* 21:7117-36 (2001), which is hereby incorporated by reference. Variants of known phosphatases can also be used including, for example, those known or suspected of being associated with a disease or condition.

Methods including a step of contacting a target compound with a kinase or phosphatase can be used to identify substrate specificity for the kinase or phosphatase, variations in kinase or phosphatase activity due to presence of an activator or inhibitor, variations in kinase or phosphatase structure that result in altered activity, or the like. In such embodiments, the target compound can be a kinase or phosphatase substrate. Furthermore, a method of the invention can be used to determine a kinase or phosphatase activity that is indicative of the presence of the kinase or phosphatase in a sample. For example, a kinase or phosphatase substrate having a known or determinable amino acid sequence can be contacted with a sample in a method of the invention and phosphorylation state of the substrate detected. Thus, the methods can be used for discovery of a kinase or phosphatase in a biological sample wherein its presence and/or activity were previously not known. Such methods can be used for diagnosis or prognosis of a disease or condition as set forth in further detail below.

A method of the invention can be used to characterize a biological sample such as a cell, tissue, organism, group of organisms, cell lysate, tissue homogenate, or fraction thereof. For example, the phosphorylation state of one or more proteins in a first system can be determined and, if desired, can be compared to the phosphorylation state of the one or more proteins of a second biological sample. Alternatively or additionally, a phosphorylation state determined for a biological sample can be compared to a phosphorylation pattern that is expected or predicted. It will be understood that, in this regard, the phosphorylation state for one or more proteins in a biological sample can be due to the activity of one or more different kinases or phosphatases. Accordingly, the invention can be used to identify the complement of active kinases or phosphatases in a particular biological sample. For example, a biological sample can produce a particular signature of phosphorylated protein or proteins that indicates the complement of active kinases or phosphatases.

If desired one or more kinase, phosphatase or target protein can be isolated from a biological sample for use in a method of the invention, for example, using methods set forth previously herein. However, a biological sample used in a method described herein, can be a complex mixture of kinases, phosphatases or target proteins. Thus, the methods can be carried out in a multiplex fashion with respect to having multiple kinases, phosphatases, target proteins or a combination thereof. For example, multiple kinases and/or phosphatases can be contacted with multiple target compounds in a multiplex format. In such a case, modification of the target proteins can be detected using an array to differentiate individual target proteins from each other, for example, using methods exemplified in Example I.

As a further example, a method of the invention can be used to separately evaluate the kinase or phosphatase activity of a biological sample toward one or more individual target substrates (i.e. target of a kinase and/or phosphatase). More specifically, one or more target compounds can be contacted with a biological sample, or fraction thereof, under conditions in which one or more kinases are capable of phosphorylating their substrates. The kinase activity can then be determined based on detection of the phosphorylation state of one or more of the target compounds. Similarly a phosphorylated target compound can be added to a biological sample under conditions in which one or more phosphatases is capable of removing the phosphate.

The ability to perform a multiplexed kinase and/or phosphatase assays in accordance with the invention provides an advantage for the evaluation of signal transduction cascades or other biochemical pathways that are influenced by multiple kinases and/or phosphatases. A multiplexed assay can more closely mimic the complexities of biological systems such that evaluation of the results can yield observations and information that is different or absent when the results of individual assays, using the components of the multiplexed assay, are evaluated alone.

A method of the invention can be used to separately evaluate the effect of an inhibitor or activator on the kinase or phosphatase activity of a biological sample. More specifically, one or more target compounds can be contacted with a biological sample, or fraction thereof, under conditions in which one or more kinases are capable of phosphorylating their substrates. A similar sample can be prepared that additionally includes an agent that is a known inhibitor (or activator) or candidate inhibitor (or activator) of at least one of the kinases. The kinase activity can then be determined in both samples based on detection of the phosphorylation state of one or more of the target compounds. The effects of a known or candidate inhibitor (or activator) of a phosphatases can be determined by a similar sample comparison.

An activity of a kinase or phosphatase determined in a method of the invention can include one or more characteristic. For example, the amino acid sequence of a protein target that is phosphorylated or dephosphorylated can be determined and, if desired, the location where phosphorylation or dephosphorylation occurs can also be identified. Such evaluations can be used to determine specificity of a kinase or phosphatase for a particular amino acid sequence. The amino acid recognition sequence identified in a method of the invention can be a discreet sequence or a consensus sequence, having one or more degenerate position. In embodiments employing multiple target proteins, the target proteins can have different amino acid sequences such that identification of those sequences that are modified by a kinase or phosphatase, those that are not substantially modified by the kinase or phosphatase, or both can be used to determine the sequence specificity of the kinase or phosphatase.

Activity of a kinase or phosphatase can be determined qualitatively or quantitatively in a method of the invention. Exemplary qualitative determinations can include, without limitation, identification of substrate specificity; identification of conditions that increase or decrease activity; determination of the presence or absence of activators or inhibitors of the kinase or phosphatase; or determination of relative activities between different samples, kinases, phosphatases, target compounds or conditions. Quantitative determinations can be made for these or other characteristics for a more precise measure, if desired. For example, a method of the invention can be used to determine the binding affinity of a kinase or phosphatase for a particular target compound in the form of a thermodynamic constant, such as a dissociation constant. Similarly, an inhibition constant can be determined for a particular inhibitor in the presence of a phosphatase and its target substrate or in the presence of a kinase and its target substrate. A further quantitative measure that can be determined in a method of the invention is a catalytic rate constant for phosphorylation or removal of a phosphate. Such kinetic and thermodynamic constants can be determined using titration measurements and/or time dependent measurements in accordance with analyses known in the art as described, for example, in Segel, supra (1994), which is hereby incorporated by reference.

Exemplary biological samples that can be used in a method of the invention can include or be derived from a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*oryza saliva*), wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile; an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. A method of the invention can also be used to detect phosphorylation state, phosphatase activity or kinase activity for a prokaryote such as a bacterium, *Escherichia coli*, staphylococci or *mycoplasma pneumoniae*; an archae; a virus such as Hepatitis C virus or human immunodeficiency virus; or a viroid. A homogeneous culture or population of the above systems can be evaluated using the invention as can a collection of several different organisms, for example, in a community or ecosystem.

A cell from which one or more target compounds, phosphatases or kinases is obtained for use in the invention can be a normal cell or a cell displaying one or more symptom of a particular disease or condition. Thus, a target compound, phosphatase or kinase used in a method of the invention can be obtained from a cancer cell, neoplastic cell, necrotic cell, cell experiencing an auto-immune condition, apoptotic cell or the like. Those skilled in the art will know or be able to readily determine methods for isolating one or more target compounds, phosphatases or kinases from a cell, bodily fluid or tissue using methods known in the art such as those described above in regard to isolation of protein targets.

A method of the invention can further include steps of isolating a particular type of cell or tissue. Exemplary methods that can be used in a method of the invention to isolate a particular cell from other cells in a population include, but are not limited to, Fluorescent Activated Cell Sorting (FACS) as described, for example, in Shapiro, *Practical Flow Cytometry*, 3rd edition Wiley-Liss; (1995) (which is hereby incorporated by reference), density gradient centrifugation, or manual separation using micromanipulation methods with microscope assistance. Exemplary cell separation devices that are useful in the invention include, without limitation, a Beckman JE6™ centrifugal elutriation system, Beckman Coulter EPICS ALTRA™ computer-controlled Flow Cytometer-cell sorter, Modular Flow Cytometer™ from Cytomation, Inc., Coulter Counter™ or Channelyzer™ system, density gradient apparatus, Cytocentrifuge, Beckman J-6™ centrifuge, EPICS V™ dual laser cell sorter, or EPICS PROFILE™ flow cytometer. A tissue or population of cells can also be removed by surgical techniques. For example, a tumor or cells from a tumor can be removed from a tissue by surgical methods, or conversely non-cancerous cells can be removed from the vicinity of a tumor.

The invention can be used for diagnosis or prognosis of a disease or condition. For example, the phosphorylation state, phosphatase activity or kinase activity for a test cell or tissue that is known or suspected of being affected by a particular disease or condition can be determined using a method of the invention. If desired, phosphorylation state, phosphatase activity or kinase activity can also be determined for a second cell or tissue that serves as a control and the results from the control cell or tissue compared to the results from the test cell or tissue. A control cell or tissue can be derived from a non-affected cell or tissue from the same individual as the test cell or tissue. Alternatively, the control cell or tissue can be obtained from a separate individual. The separate individual can be a non-affected individual that is related to the test individual within one, two, three or more generations. Alternatively, the separate individual can be effectively unrelated being many generations removed, or even of a different ethnicity. In some cases it may be useful to use a control individual having similar ethnicity as the test individual.

Phosphorylation state, phosphatase activity or kinase activity determined in a method of the invention for a particular biological sample can be correlated with one or more symptoms of a disease or condition. Those skilled in the art will know or be able to determine symptoms that are indicative of a disease or condition being evaluated. An exemplary reference describing symptoms for particular diseases or conditions is *The Merck Manual of Diagnosis and Therapy* 16th Ed., Edited by Berkow, published by Merck and Co., Inc., Rahway N.J. (1992), which is hereby incorporated by reference.

A method of the invention can also be used to evaluate the effect of a particular treatment on a biological sample. The biological sample can be a cell experiencing a disease state or condition for which removal of one or more symptoms by the treatment is desired. Alternatively, the biological sample can be a normal cell for which adverse response to a particular treatment is not desired, as it represents an off-target response for the treatment. In particular embodiments, the treatment can be administration of a drug or drug candidate to a biological sample, wherein the drug or candidate drug is suspected of having an effect on the system. For example, following administration of the drug or candidate drug the phosphorylation state, phosphatase activity or kinase activity can be measured for the treated system. Thus, the invention provides a method for screening drugs or drug candidates.

A drug or drug candidate used in a method of the invention can act, for example, as a kinase inhibitor or phosphatase inhibitor, can act to increase expression of a kinase or phosphatase, or can act to destabilize one or more kinase or phosphatase, thereby reducing half life in the natural milieu. Comparison can be made to the phosphorylation state, phosphatase activity or kinase activity for a control system that has not been treated or that has been treated to a different extent. Thus, phosphorylation state, phosphatase activity or kinase activity, as measured by a method of the invention, can be used to evaluate dose response, efficacy, time period of response or the like for a biological sample undergoing a particular treatment. If available, comparison can be made to a reference activity, for example, as stored in a database or other storage medium.

The invention provides a protein having an N-acylurea moiety and a phosphoric amide moiety. Further provided is a plurality of proteins each having an N-acylurea moiety and a phosphoric amide moiety. The protein can be made for example, according to a method set forth herein. The N-acylurea moiety can include the alpha carbonyl moiety of the C-terminal amino acid of the protein, the beta carbonyl moiety of an aspartate residue or the gamma carbonyl moiety of a glutamate residue. The phosphoric amide moiety can include a label moiety, cross-linker having a reactive moiety or a linker attached to a solid-phase substrate. Thus, the protein is useful for an analytical method to identify a characteristic of the protein or a characteristic of a biological sample from which it is derived.

It will be understood that the methods exemplified above with regard to adding a nucleophilic compound to a phosphomonoester can be used to add a nucleophilic compound to other phosphorus containing moieties such as a phosphoamide or thiophosphate. Generally, the methods can be used for nucleophilic addition to a variety of electrophilic moieties that are activated by a carbodiimide compound. Furthermore, it will be understood that an electrophile-protected compound produced using a method set forth herein can be used in any of a variety of nucleophilic addition reactions, whether or not the nucleophilic addition reactions are activated by a carbodiimide compound.

The following example is intended to illustrate but not limit the present invention.

Example I

Chemical Labeling and Detection of Phosphorylated Biological Molecules

This example demonstrates a universal chemical approach for phosphorylation detection. This example further demonstrates analysis of kinase activity in a multiplex format. This example also demonstrates use of pattern recognition as a robust tool for studying kinase activity in a multiplex assay.

Assay Design

A solution-based kinase assay format was devised to demonstrate multiplexed kinase profiling on the Sentrix® BeadArray platform as schematically represented in FIG. 2. In order to make the assay compatible with the Sentrix® BeadArray readout, protein (also referred to as "peptide") substrates for the kinases were modified into DNA-conjugated protein targets. Each different protein sequence was conjugated to a unique DNA sequence and each DNA sequence was complementary to a unique DNA probe of the array. Thus, following hybridization of the DNA-conjugated proteins to the array, each protein target can be identified according to its location on the array.

As shown in FIG. 2, a kinase recognizes the protein portion of a DNA-protein conjugate and phosphorylates the protein at a specific site in the amino acid sequence resulting in a phosphorylated protein, in solution. A label molecule (fluorescent dye or biotin) containing an amino moiety is then reacted with the phosphomonoester moiety of the protein, also in solution. The DNA-protein conjugate is incubated with the Sentrix® BeadArray and the DNA moiety is hybridized to its complementary DNA on the array. Presence or absence of signal from the label at each probe location is detected. The presence of signal at a specific probe location indicates that the respective protein moiety conjugated to the probe complement is phosphorylated.

Phosphorylated proteins were detected using the universal chemical approach shown in FIG. 1. As shown in FIG. 1B, a dye label having an amino moiety can be covalently attached to a phosphate moiety by activating nucleophilic attack of the amine on the phosphomonoester with 1-Ethyl-3-(3-dimethylaminopropyl)-carbodiimide (EDC, Fluka) at pH 7.5. However, carboxylic moieties are also reactive under these conditions. As shown in FIG. 1A, an EDC molecule adds to the carbonyl to form an O-acylurea derivative that is subject to nucleophilic attack by the amino-containing dye when activated by a second EDC molecule. This can result in unwanted labeling of a protein target at free carbonyls of aspartic acid, glutamic acid and protein c-termini. Carbonyls were blocked (i.e. protected) from subsequent dye-labeling by pre-treating the protein with EDC at pH 4.5 for 90 mins. The pre-treatment is believed to form O-acyl derivatives at carbonyls which rearrange to form stable N-acylurea derivatives of the carbonyls, as shown in FIG. 1A and as described in Toniolo et al., *Helvetica Chimica Acta,* 73:626 (1990), which is hereby incorporated by reference. Following pretreatment, the protein can be reacted with EDC and the amino containing dye at pH 7.5 such that N-acylated carbonyls are not reactive to amino-containing dye (as shown in FIG. 1A) and phosphorylated amino acids are selectively labeled (as shown in FIG. 1B).

Synthesis of Protein-DNA Conjugates

A DNA molecule having a benzaldehyde nucleotide at the 3' end was synthesized using methods described in U.S. Ser.

No. 10/739,959, which is hereby incorporated by reference. The benzaldehyde residue on the DNA was coupled to an aminooxyacetic moiety on the amino terminus of a protein, at pH between 4.0 and 5.5, to form an oxime bond as described in U.S. Ser. No. 11/090,904, which is hereby incorporated by reference.

Specificity of Phosphate Detection Using Chemical Labeling

FIG. 3 shows the results of dye-labeling of proteins with and without EDC pre-treatment. R1 was a protein target containing a tyrosine residue, R2 had the same sequence as R1, however, the tyrosine residue was phosphorylated synthetically; R3 was a protein target containing a serine residue; R4 had the same sequence as R3, however, the serine residue was phosphorylated synthetically; R5 was a protein target containing an aspartic acid residue; R6 had a glutamic acid residue.

As shown in FIG. 3, when the proteins were reacted with amino-containing dye and EDC at pH 7.5, following pretreatment at pH 7.5 without EDC (identified as "pH 7.5" in the Figure) the R5 and R6 targets, which contained carbonyl moieties but no phosphate moieties were labeled along with the phosphorylated targets R2 and R4. Similar reactivity of free carbonyls resulted when the proteins were pretreated with EDC at pH 7.5 (labeled "pH 7.5, EDC pretreatment" in the Figure) or when the proteins were pretreated at pH 4.5 in the absence of EDC ("pH 4.5"). However, when the proteins were pretreated with EDC at pH 4.5, targets R2 and R4, having phosphomonoester, were labeled, whereas targets R5 and R6, having carbonyls but no phosphomonoesters were blocked from being labeled. The data demonstrates that specific detection of phosphorylated protein was achieved using low pH, EDC pre-treatment followed by EDC activated amino-dye labeling at neutral pH.

Correlation of Antibody Labeling and Chemical Labeling Methods

A kinase profiling assay was carried out in four major steps, including the phosphorylation of protein target in a kinase enzyme reaction, labeling of phosphorylated target, hybridization of labeled target to the array, and detection of hybridized target on the array.

In the first step, phosphorylation was carried out in duplex format such that a mixture of two DNA-protein conjugate targets, one having an amino acid recognition sequence for p60c-src kinase and the other for PKA kinase, were co-incubated with p60c-src kinase and PKA kinase. The reaction was performed in 15 ul of 50 mM HEPES, containing 0.1 mM EDTA, 0.015% Brig 35, 0.15 mM ATP, 30 mM $MgCl_2$, 0.1% 2-mercaptoethanol, pH 7.5.

Upon completion of the enzymatic reaction; the second step was carried out to detect phosphorylation using chemical labeling or antibody-based labeling. In the chemical labeling method, a solution of 5-(aminoacetamido)fluorescein (NH2-FAM, Molecular Probes, Oreg.) and EDC in MES buffer, pH 6.0, was added to the reaction mixture to a final concentration of 150 mM EDC and 200 µM of NH2-FAM. Where pre-treatment was used to block (i.e. protect) carbonyl moieties, the pH of the reaction mixture was first adjusted to pH 4.5 and then pre-treated with 100 mM of EDC for 1.5 hours at 25° C. After the pre-treatment, the NH2-FAM and EDC were added and the reaction was allowed to proceed overnight. Where antibodies were used as detection reagents for phosphotyrosine, a mouse anti-phosphotyrosine-biotin conjugate (Upstate Cell Signaling Solutions, Va.) was used along with a streptavidin, R-phycoerythrin conjugate (Molecular Probes, Oreg.). For phosphoserine detection, five different biotinylated antibodies were tested each in combination with a streptavidin, R-phycoerythrin conjugate.

In the third step, the mixture from the labeling step was diluted into GoldenGate™ hybridization buffer (Illumina, Inc., San Diego, Calif.) to a final concentration of 100 pM DNA-protein conjugate target and hybridized onto a Sentrix® BeadArray Matrix for 24 hours at room temperature. The BeadArray matrix included nucleic acid probes that were complementary to the DNA portion of the DNA-protein conjugate targets.

In the fourth step, the array was washed and then imaged using the Ultra Scanner (Illumina, Inc., San Diego, Calif.) set at 485 nm excitation and 535 nm emission to detect the presence of fluorescein on the probes.

Seven different duplex assays were carried out, each with different p60c-src and PKA kinase concentrations. Following the phosphorylation step, each solution was divided into two samples for phosphorylation detection. The first detection sample was evaluated using the EDC chemical detection method (FIG. 4A), the other was evaluated using anti-phosphotyrosine and anti-phosphoserine antibodies (FIG. 4B). As shown in FIG. 4A, a saturable increase in kinase activity was observed when the chemical labeling method was used to monitor kinase titration of either kinase. A similar saturable response was observed using an anti-phosphotyrosine antibody to detect the p60c-src kinase substrate (which is expected to be phosphorylated at a tyrosine residue by the p60c-src kinase). An 89% correlation between the antibody based and the universal chemical detection methods was achieved for detection of p60c-src kinase activity. The anti-phosphoserine antibody failed to detect the phosphorylation of the PKA substrate that was detected using the chemical labeling method.

Kinase Profiling Assay Results Using the p60c-src and PKA Systems

The kinase profiling assay was carried out using the four step method as set forth above with the following modifications. The enzymatic step was performed in solution using nanomolar amounts of kinase enzyme and multiplexed protein target pools having 6, 96, 100, or 194 different protein targets. Upon completion of the enzymatic reaction, the chemical labeling method was used, including low pH, EDC pre-treatment, to detect both phosphotyrosine and phosphoserine residues.

For the inhibition studies, Src Kinase Inhibitor I and Protein Kinase A Inhibitor 6-22 Amide were used as the inhibitors for the p60c-src kinase and PKA kinase, respectively (Calbiochem, Calif.).

Results for the 194-target pool are shown in FIG. 5. The p60c-src and PKA substrates were phosphorylated selectively by p60c-src and PKA kinases; p60c-src and PKA were inhibited selectively by their corresponding inhibitors. The p60c-src and PKA substrates were mixed with 48 targets containing a tyrosine residue, 48 targets containing a serine residue, and 96 targets containing synthetically phosphorylated tyrosine or serine residues. All the 96 non-phosphorylated targets showed signals equivalent to background, and all the 96 phosphorylated targets showed signals comparable to p60c-src and PKA substrates. Similar data was also obtained using pools of 6 or 100 targets.

FIG. 6 summarizes results for the 194-target pool. Cross reactivity for p60c-src and PKA was less than 1%. Furthermore, selective inhibition of enzymatic activity of each kinase was observed. Specifically, Src Kinase Inhibitor I showed 85% inhibition of p60c-src kinase while having no detectable effect on PKA kinase and Protein Kinase A Inhibitor 6-22 Amide showed greater than 99% inhibition of PKA while having no detectable effect on p60c-src kinase.

Figure 7A:
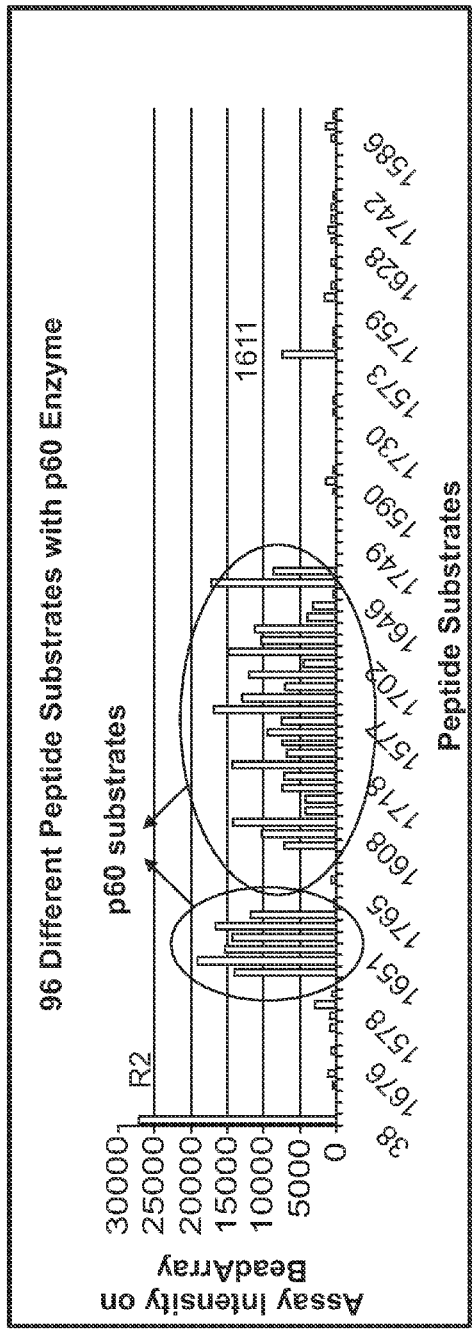
Figure 7B:
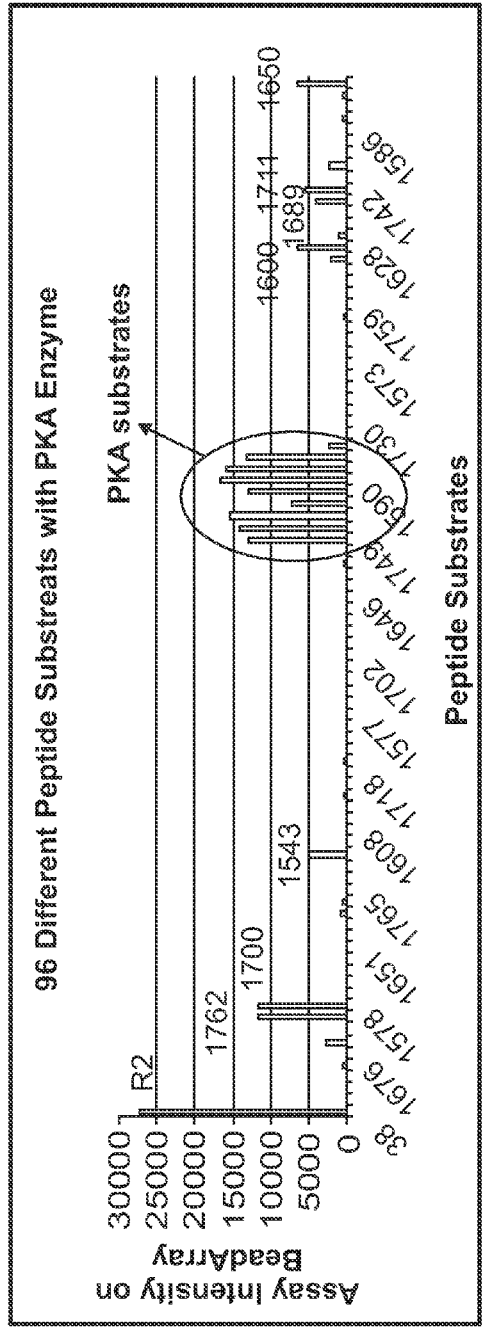

To demonstrate the robustness of the universal detection method, a series of control targets were made containing amino acid residues that could potentially interfere with the labeling method. The control targets included substrates for other kinases, such as PKC, CAMKII, Abl, ERK, that are not typically phosphorylated by p60c-src and PKA kinases. As shown in FIG. 7, substrates for p60c-src kinase (circled in FIG. 7A) and substrates for PKA kinase (circled in FIG. 7B) showed high signal. The low background signal observed for the control targets in FIG. 7 indicates that the chemical labeling method is specific for the phosphomonoester moiety.

To confirm that free carboxylic acid moieties did not interfere with the chemical labeling method, R5 (having an aspartic acid residue) and R6 (having a glutamic acid residue) were mixed with the 96-target pool and the four step assay repeated. The low pH, EDC pre-treatment was used before the phosphomonoester labeling. Decreased R5 and R6 signals were observed while signal obtained for other targets were similar to the data shown in FIG. 7.

Figure 8A:
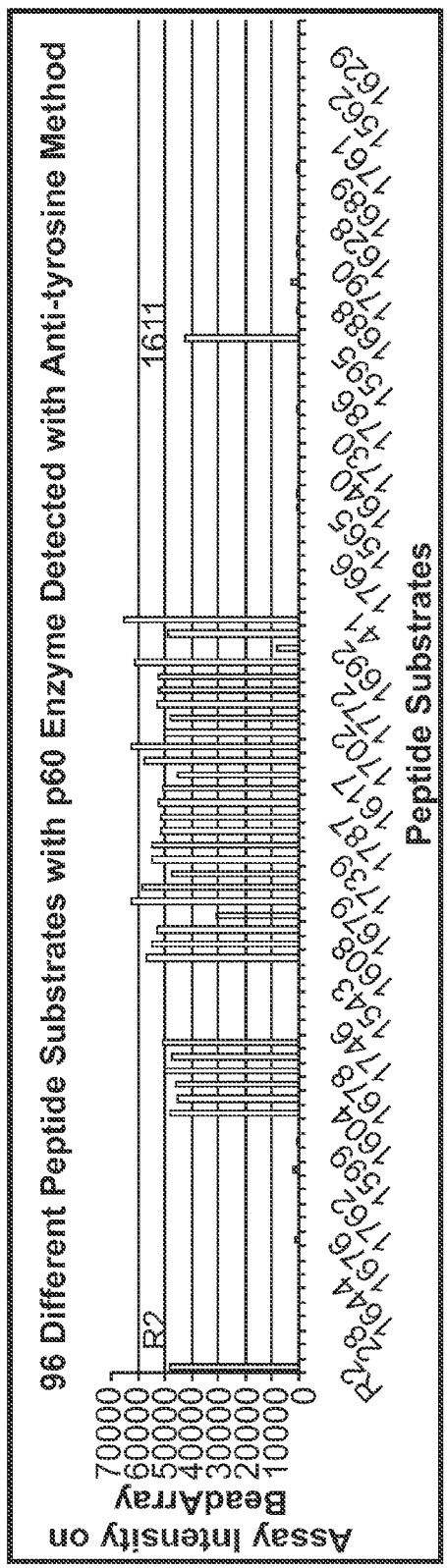
Figure 8B:
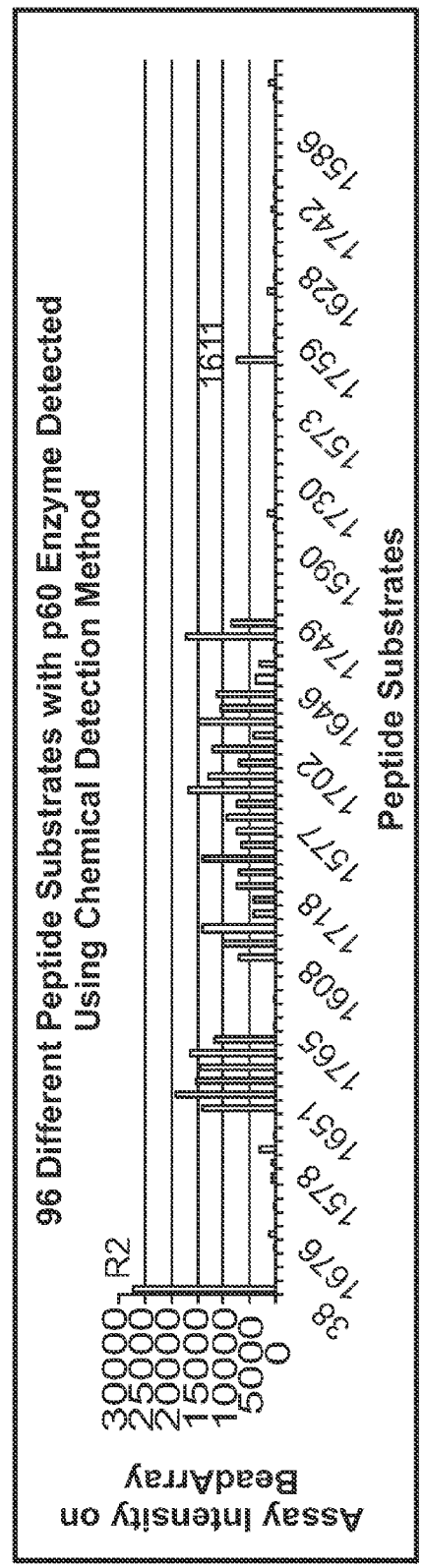

To further demonstrate the reliability of the chemical labeling method, the anti-phosphotyrosine antibody was used side by side with the universal detection method. FIG. 8A shows the results of antibody labeling, and FIG. 8B shows the results of the chemical labeling method. 100% correlation was obtained using pair wise signal comparisons for targets yielding positive phosphorylation intensities in chemical and antibody labeling methods. The results demonstrate that both detection methods correlated well.

Pattern Recognition as a Tool for Evaluating Kinase Activity

Data sets obtained from multiplex kinase assays can be quite complex, and in some cases, difficult to evaluate using a standard bar graph. The difficulty can be acerbated when comparing the phosphorylation state of a panel of multiple targets resulting, from different treatments such as exposure to different kinases and/or kinase inhibitors. In such cases, it is helpful to represent the data in a format that is readily distinguishable by pattern recognition. A representation that is convenient for pattern recognition by eye is a "star plot." A star plot is comparable to a bar graph except that the bars occur in a radial pattern, about a circular axis, rather than along a linear axis. Signal from each target appears as a spoke and the quantitative amount of signal is correlated to the length of the spoke.

FIG. 9 shows exemplary star plots for several kinases individually evaluated for the ability to phosphorylate targets in the same mixture of 96 different protein-DNA targets. For each star plot, the 96 targets are plotted in the same order and starting with the same target at the 12 O'clock position. Absence of a spoke indicates that no signal was detected for the particular target. Where a spoke is present, its length indicates the intensity of the signal, which is proportional to the level of phosphorylation of the target. As shown in FIG. 9, the pattern of activity is unique for each kinase and can be readily determined by eye. Comparison of the star plot for each kinase indicates that the target mixture contains specific protein substrates for each kinase enzyme.

FIG. 10 shows an example of the data obtained by testing two kinases (p60c-src and PKA) with the target mixture containing 96 different protein-DNA targets and in the presence or absence of different kinase inhibitors. Plots 1 and 2 of FIG. 10 show the signals obtained for phosphorylation of the target mixture with p60c-src and PKA, respectively. Plot 3 of FIG. 10 combines the data from plots 1 and 2, demonstrating the ease with which the individual kinase patterns can be recognized when combined. As shown in plots 4 and 5 of the figure, selective inhibition of enzymatic activity of each kinase was observed. As shown in plots 6 and 7 of FIG. 10, inclusion of an inhibitor targeting either p60c-src or PKA, in the dual-enzyme mixture, removed signal from the expected target enzyme and restored the star plots to the same pattern as the non-targeted enzyme.

Throughout this application various publications, patents and patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the invention has been described with reference to the examples provided above, it should be understood that various modifications can be made without departing from the invention. Accordingly, the invention is limited only by the claims.

What is claimed is:

1. A method of modifying a target compound, comprising
   (a) providing a target compound comprising a carboxylic acid moiety and a phosphomonoester moiety;
   (b) reacting the carboxylic acid moiety of the target compound with a first carbodiimide compound to form an N-acylurea moiety on the target compound, thereby forming a carboxyl-protected target compound, wherein the carboxyl-protected target compound comprises the N-acyl urea moiety and the phosphomonoester moiety; and
   (c) reacting the phosphomonoester moiety of the carboxyl-protected target compound with a second carbodiimide compound and an amine compound to form a phosphoric amide moiety on the carboxyl-protected target compound.

2. The method of claim 1, further comprising a step of (d) detecting the phosphoric amide moiety.

3. The method of claim 1, wherein the amine compound comprises a label moiety.

4. The method of claim 3, wherein the phosphoric amide moiety comprises the label moiety.

5. The method of claim 4, further comprising a step of (d) detecting the label moiety of the phosphoric amide moiety.

6. The method of claim 1, wherein the target compound comprises a protein.

7. The method of claim 6, further comprising identifying the type of amino acid that is attached to the phosphoric amide moiety.

8. The method of claim 6, further comprising identifying the primary sequence location of an amino acid that is attached to the phosphoric amide moiety.

9. The method of claim 6, wherein the N-acylurea moiety comprises the alpha carboxylic acid moiety of the C-terminal amino acid of the protein, the beta carboxylic acid moiety of aspartate or the gamma carboxylic acid moiety of glutamate.

10. The method of claim 6, wherein the phosphoric amide moiety is selected from the group consisting of phosphoserine, phosphothreonine, and phosphotyrosine.

11. The method of claim 6, wherein step (a) further comprises contacting the protein with a kinase under conditions for producing the phosphomonoester moiety of the protein.

12. The method of claim 11, further comprising identifying a phosphorylation activity of the kinase from the phosphoric amide moiety of the carboxyl-protected target compound.

13. The method of claim 11, wherein the protein is contacted with the kinase in the presence of a kinase inhibitor or a kinase activator.

14. The method of claim 13, further comprising identifying inhibition or activation of phosphorylation activity of the kinase from the phosphoric amide moiety of the carboxyl-protected target compound.

15. The method of claim 1, wherein the carbodiimide compound is EDC.

16. The method of claim 1, wherein the amine compound is attached to a solid support.

17. The method of claim 1, wherein the first carbodiimide compound and the second carbodiimide compound comprise the same molecular species.

18. The method of claim 1, wherein the first carbodiimide compound is contacted with the target compound in a reaction vessel and the second carbodiimide compound is contacted with the carboxyl-protected target compound in the reaction vessel.

19. The method of claim 18, wherein the first carbodiimide compound and the second carbodiimide compound are simultaneously added to the reaction vessel.

20. The method of claim 1, wherein the phosphoric amide moiety is attached to a solid support.

* * * * *